United States Patent [19]

Christensen et al.

[11] 4,260,627
[45] Apr. 7, 1981

[54] 1-, 6- AND 2-SUBSTITUTED-1-CARBA-2-PENEM-3-CARBOXYLIC ACIDS

[75] Inventors: Burton G. Christensen, Metuchen; David H. Shih, Edison, both of N.J.

[73] Assignee: Merck & Co., Inc., Rahway, N.J.

[21] Appl. No.: 954,271

[22] Filed: Oct. 24, 1978

[51] Int. Cl.³ .................. C07D 487/04; A61K 31/40
[52] U.S. Cl. ................. 424/274; 260/239 A; 260/245.2 T; 424/250; 424/263; 424/269; 424/270; 424/273 P; 424/273 N; 542/453; 544/90; 544/333; 546/272
[58] Field of Search ............. 260/326.7, 245.2 T; 424/274, 269, 270, 263, 273 P, 273 N, 250; 542/453; 546/272; 544/333

[56] References Cited
U.S. PATENT DOCUMENTS 3,950,357  4/1976  Kahan ................. 260/245.2 T

*Primary Examiner*—Mary C. Lee
*Attorney, Agent, or Firm*—James A. Arno; Julian S. Levitt

[57] ABSTRACT

Disclosed are 1-, 6- and 2-substituted-1-carba-2-penem-3-carboxylic acids of the following structure:

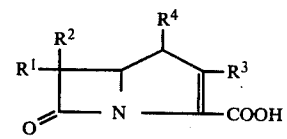

wherein $R^1$, $R^2$, $R^3$ and $R^4$ are, inter alia, independently selected from the group consisting of hydrogen, alkyl, aryl, and aralkyl. Such compounds as well as their pharmaceutically acceptable salt, ester and amide derivatives are useful as antibiotics. Also disclosed are processes for the preparation of such compounds, pharmaceutical compositions comprising such compounds and methods of treatment comprising administering such compounds and compositions when an antibiotic effect is indicated.

6 Claims, No Drawings

1-, 6- AND 2-SUBSTITUTED-1-CARBA-2-PENEM-3-CARBOXYLIC ACIDS

BACKGROUND OF THE INVENTION

This invention relates to 1-, 6- and 2-substituted-1-carba-2-penem-3-carboxylic acids (I) which compounds and their pharmaceutically acceptable salts and esters are useful as antibiotics:

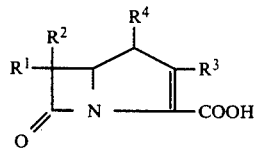

wherein $R^1$, $R^2$, $R^3$ and $R^4$ are independently selected from the group consisting of hydrogen, substituted and unsubstituted: alkyl, alkenyl, alkynyl, cycloalkyl, cycloalkylalkyl, alkylcycloalkyl, aryl, aralkyl, aralkenyl, aralkynyl, heteroaryl, heteroaralkyl, heterocyclyl and heterocyclylalkyl wherein the substituent or substituents relative to the above named radicals are selected from the group consisting of amino, hydroxy, alkoxyl, mercapto, alkylthio, arylthio, sulfamoyl, amidino, guanidino, nitro, chloro, bromo, fluoro, cyano and carboxy; and wherein the hetero atom in the above-named heterocyclic moiety is selected from the group consisting of oxygen, nitrogen and sulphur.

This invention also relates to the pharmaceutically acceptable salt, ester and amide derivatives of the compounds of the present invention identified by structure I, above.

The invention also relates to processes for the preparation of such compounds (I); pharmaceutical compositions comprising such compounds; and to methods of treatment comprising administering such compounds and compositions when an antibiotic effect is indicated.

There is a continuing need for new antibiotics. For unfortunately, there is no static effectiveness of any given antibiotic because continued wide scale usuage selectively gives rise to resistant strains of pathogens. In addition, the known antibiotics suffer from the disadvantage of being effective only against certain types of microorganisms. Accordingly the search for new antibiotics continues.

Thus, it is an object of the present invention to provide a novel class of antibiotics which are useful in animal and human therapy and in inanimate systems. These antibiotics are active against a broad range of pathogens which representatively include both gram positive bacteria such as *S. aureus, Strep. pyogenes,* and *B. subtilis,* and gram negative bacteria such as *E. coli, Pseudomonas, Proteus morganii,* Serratia and Klebsiella. Further objects of this invention are to provide chemical processes for the preparation of such antibiotics and their non-toxic pharmaceutically acceptable salts; pharmaceutical compositions comprising such antibiotics; and to provide methods of treatment comprising administering such antibiotics and compositions when an antibiotic effect is indicated.

DETAILED DESCRIPTION OF THE INVENTION

The compounds of the present invention (I, above) are conveniently prepared by the following scheme:

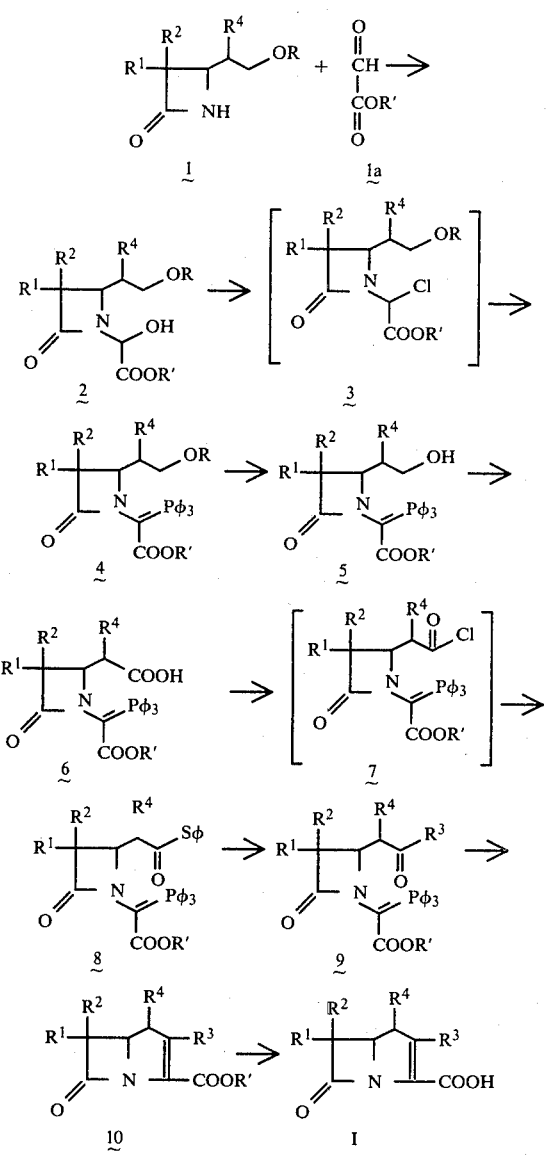

wherein $R^1$, $R^2$ and $R^3$ are as defined; R and R' are readily removable blocking groups; R' may also be a pharmaceutically acceptable ester moiety. Typically, the blocking group R is an acyl such as a lower alkanoyl, aralkylcarbonyl or the like such as acetyl, bromo-t-butoxycarbonyl, benzyloxycarbonyl, formyl, trifluoroacetyl and the like or a trialkylsilyl such as trimethylsilyl or t-butyl dimethylsilyl group; and typically the blocking group R' is substituted or unsubstituted alkyl, aralkyl, alkenyl, or the like such as benzyl, p-nitrobenzyl, o-nitrobenzyl, pivaloyloxymethyl, bromo-t-butyl and the like.

In words relative to the above reaction diagram, a suitably substituted azetidinone (1) is reacted with a glyoxylate ester such as benzyl glyoxalate to form the corresponding 1-(benzyloxycarbonylhydroxymethyl- )azetidinone (2). The reaction 1→2 is conveniently carried out in a solvent such as benzene, toluene, xylene and the like at a temperature of from about 25° C. to reflux for from 2 to 10 hours. There is no criticality as to the precise identity of the solvent, provided only that it adequately solubilizes the reactants and be inert or substantially inert to the desired course of reaction. The halogenation reaction 2→3 may be conducted by any of any of a variety of well-known halogenation means. Suitable reagents include: $SOCl_2$, $POCl_3$, oxalyl chloride and the like. A preferred menas of chlorination involves treating 2 in a solvent such as tetrahydrofuran (THF), ether, $CH_2Cl_2$ and the like with thionylchloride in the presence of 1 to 2 equivalents (relative to the thionylchloride) of a base such as pyridine, triethylamine, quinoline and the like. Typically, the reaction is conducted at a temperature of from −30° to 25° C. for from 0.5 to 1 hour. The resulting 1-(benzyloxycarbonyl-chloromethyl)-azetidinone species, 3, is isolated, if desired, by conventional procedures for later reaction, 3→4. The intermediate 4 is prepared form 3 by treating 3 in a solvent such as dimethylformamide (DMF), dimethylsulfoxide (DMSO), THF, dimethoxyethane (DME) and the like with 1 to 1.5 equivalents of a phosphine such as triphenylphosphine, tributylphosphine, triethylphosphine, tris-(2-cyanoethyl)phosphine or the like. Typically the reaction is conducted under a nitrogen atmosphere at a temperature of from −20° to 25° C., for from 0.5 to 2 hours. The reaction 4→5 may be achieved by any of a variety of well-known deblocking procedures such as hydrolysis or hydrogenolysis. A particularly convenient means for the deblocking 4→5, is by an alcoholysis procedure comprising treating 4 in a lower alkanol such as methanol, ethanol, or the like in the presence of 0.1 to 1.4 equivalents of the corresponding alkali metal alkoxide such as sodium methoxide or the like; typically the reaction is conducted at a temperature of from 0° to 25° C., for from 0.5 to 2 hours. Oxidation of 5→6 may be achieved by treating 5 with an oxidizing system such as $CrO_3/H_2SO_4/Me_2O$ (Jones' reagent), $RuO_4/CCl_4$, $KMnO_4/H_2O$, t-butyl chromate or the like. Preparation of 9 from 6 may be achieved by well known methods for converting a carboxylic acid to a ketone such as by activating a carboxylic function with dicyclohexylcarbodiimide, ethylchloroformate, 2-fluoropyridine, 1-fluoro-2,4-dinitrobenzene, thionyl chloride, oxalyl chloride, or the like followed by the neucleophilic displacement of the leaving group with a carbon neucleophiles such as RMgX, $LiCuR_2$, $R_2Cd$ or the like to give the desired ketone 9. Or preferably by treating 6 with oxalyl chloride followed by neucleophilic displacement of the chloride with a thiophenol to give a stable thioester 8 which may subsequently be reacted with a Grignard reagent to yield the ketone 9. Typically, the closure step 9→10 is conducted by heating from 100°–160° C. in a solvent such as benzene, toluene, dioxane, xylene, or DMF. The carboxyl deblocking step 10→(I) may be achieved by a number of well-known procedures such as hydrolysis, hydrogenation, or photolysis of a suitable R′ group. Suitable hydrogenation catalysts for deblocking include the platinum metals and their oxides such as palladium on carbon and the like; suitable solvents for the hydrogenation include methanol, dioxane/$H_2O$, ethanol/$H_2O$ and the like in the presence of hydrogen at a pressure of from 1 to 50 atmospheres; the hydrogenation is typically conducted for from 5 min. to 4 hours at a temperature of about 25° C. in the optional presence of a mild base such as sodium bicarbonate or the like.

The glyoxalate esters 1a used to react with 1 can be prepared by oxidation of the corresponding tartaric acid diesters with oxidants such as periodic acid or lead tetracetate in a solvent such as THF, benzene, methylene chloride at −20° to 25° for ½ to 4 hours. The tartarate esters are prepared from dilithio tartarate or disodio tartarate by reaction with R′X wherein X is chloro, bromo or iodo and R′ is as defined above in a solvent such as DMF or DMSO at 25° to 70° C. for from 4 to 48 hours. As noted above, R′ may be a pharmaceutically acceptable esters and amides, however, may also be prepared from the free acid of I according to the procedure of co-pending U.S. patent application Ser. No. 733,651 filed Oct. 18, 1976, now abandoned which is directed to the pharmaceutically acceptable esters and amides of thienamycin and their preparation. Accordingly, for its disclosure relative to such pharmaceutically acceptable forms and their means of preparation, the above-cited application is incorporated herein by reference.

The substituted azetidinone 1 is disclosed and claimed in co-pending, U.S. patent application Ser. No. 743,370, Bouffard et al. now abandoned, which application is incorporated herein by reference for the disclosure relative to 1 and its preparation. The following diagram summarizes the synthesis of this essential starting material, 1.

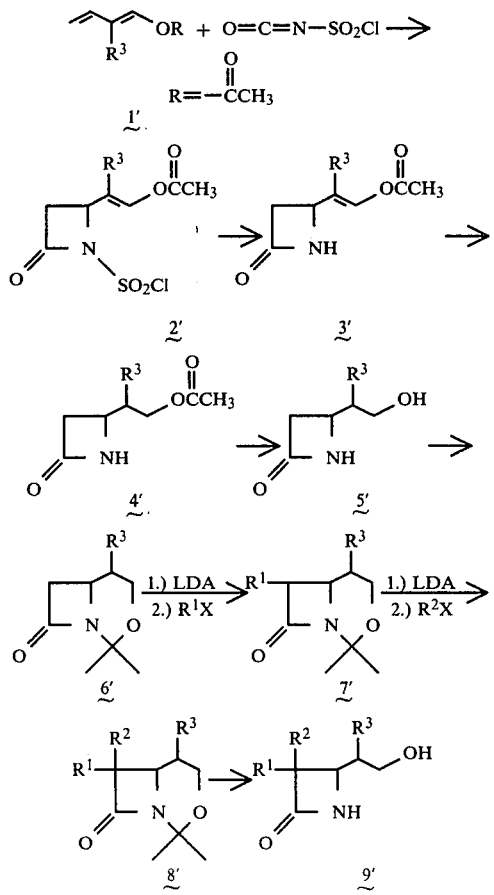

-continued

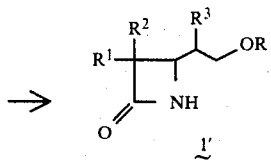

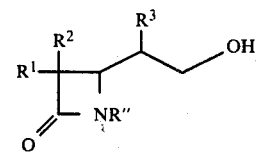

In words relative to the above diagram for the preparation of 1 the 4-(1-methyl-2-acetoxyvinyl)azetidinone-2-one (3') is prepared by reacting chlorosulphonyl isocyanate and an acyloxybutadiene (1') such as 1-acetoxy-2-methylbutadiene in a solvent such as anhydrous diethyl ether at a temperature of from about −30° C. to 0° C. under a nitrogen atmosphere. The reaction intermediate 2' is converted to 3' by hydrolysis. The reduction of 3' to provide the 4-(1-methyl-2-acetoxyethyl)-2-azetidinone (4') is conducted by any convenient means such as hydrogenation in the presence of a catalyst such as platinum, palladium or oxides thereof under a hydrogen pressure of from 1 to 20 atmospheres in a solvent such as ethanol, ethylacetate, or the like at a temperature of from 0° to 25° C., for from 5 minutes to 1 hour. The 4-(2-hydroxy-1-methylethyl-2-azetidinone species 5' is obtained from 4' by hydrolysis. The 8-oxo-2,2,5-trimethyl-3-oxa-1-azabicyclo[4.2.0]octane species 6' is obtained on treatment of 5' with 2,2-dimethoxypropane in the presence of a catalyst such as boron trifluoride etherate in a solvent such as methylene chloride at a temperature of from 0° to 40° C. for from 1 to 40 minutes. Alternatively, 5' can be treated with boron trifluoride etherate and trimethylorthoformate to give 8-oxo-2-methoxy-5-methyl-3-oxa-1-azabicyclo[4.2.0]octane which can be mono- or dialkylated following the procedures for 6' 7' or 8'. Alkylation of 6' provides 7'. Typically, 6' is treated with a strong base such as lithium diisopropylamide, sodium hydride, phenyl lithium or butyl lithium and the like in a solvent such as tetrahydrofuran (THF), ether, dimethoxyethane and the like at a temperature of from −80° C. to 0° C., whereupon the alkylating agent of choice, R¹X is added (R¹ is as described above and X is chloro or bromo; alternatively the alkylating agent may be R¹-tosylate, R¹-mesylate or an aldehyde or ketone such as acetaldehyde and the like) to provide mono- alkylated species 7'. When desired dialkylated species 8' may be obtained from 7' by repeating the alkylating procedure, 6'→7'. Species 9' is obtained from 7' or 8' by acid hydrolysis.

The desired blocked-species 1 is obtained by treating 9' with an silylating agent such as t-butyldimethylchlorosilane, trimethylchlorosilane and the like in a solvent such as DMF, CH₂Cl₂, THF or the like in the presence of a base such as imidazole or the like at 0° C. to 25° C. for from 0.5 hr to 6 hr or with an acylating agent such as acetyl chloride, formic acetic anhydride, trifluoroacetic anhydride and the like in a solvent such as CH₂Cl₂, CHCl₃, THF and the like at a temperature of from −20° to about 25° C. for from 0.5 to about 4 hours. The starting material 1 may be isolated for later reaction in accordance with the procedures of the present invention for the preparation of the compounds of the present invention.

It should be noted that in the establishment of R (9'→1), the ring nitrogen may be protected by an easily removable blocking group R'':

wherein R'' is acyl or triorganosilyl such as trimethylsilyl, t-butyldimethylsilyl, trifluoroacetyl, formyl, or the like. Removal of R'' is accomplished by hydrolysis to provide 1 according to well-known procedures.

Starting material 1, may alternatively be prepared by the following scheme:

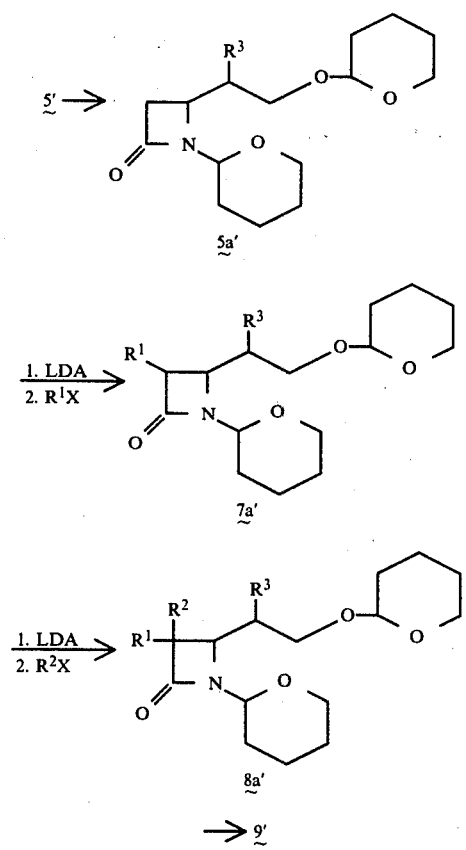

wherein all symbolism is as previously defined.

Reaction 5'→5a' is accomplished by treating 5' with 2,3-dihydropyran in a solvent such as p-dioxane benzene, and the like in the presence of p-toluene-sulfonic acid, perchloric acid, or the like at a temperature of from 0° to about 30° C. The intermediate 5a' may be isolated for later alkylation to obtain 7a' and 8a' by procedures analogous to previously described reactions 6'→7'→8'. Intermediate species 9' is obtained from 7a' or 8a' by mild acid hydrolysis.

Finally, it should be noted that intermediate species 9a' may conveniently be prepared for later reaction in the above scheme by internal acylation according to the following reaction:

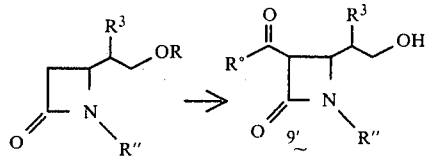

wherein R is acyl,

is $R^1$ and $R°$ is for example, lower alkyl, acyl, or the like. Typically, the above reaction is conducted in a solvent such as tetrahydrofuran, ether, dimethoxyethane, or the like in the presence of 1 to 2 equivalents of a strong base such as lithium diisopropylamide, sodium hydride, potassium hydride or the like at a temperature of from $-78°$ to $25°$ C., for from 0.5 to 24 hours.

In the generic description of the present invention (I, above), the substituents $R^1$, $R^2$ and $R^3$ are preferably selected from the group consisting of hydrogen; substituted and unsubstituted: straight and branched loweralkyl having from 1 to 10 carbon atoms; cycloalkyl having from 3 to 6 carbon atoms; cycloalkylalkyl wherein the cycloalkyl moiety comprises 3 to 6 carbon atoms and the alkyl moiety comprises 1 to 10 carbon atoms; alkylcycloalkyl wherein the alkyl moiety comprises 1 to 6 carbon atoms and the cycloalkyl moiety comprises 3 to 6 carbon atoms; aryl such as phenyl and naphthyl; aralkyl such as benzyl, phenethyl and the like; heterocyclyl (saturated and unsaturated) comprising mono- and bicyclic structures having from 5 to 10 ring atoms wherein one or more of the hetero atoms is selected from oxygen, nitrogen or sulphur, such as thiophene, imidazolyl, tetrazolyl, furyl and the like; heterocyclylalkyl which comprises the immediately preceding heterocyclyl moieties and the alkyl moiety comprises from 1 to 10 carbon atoms; the substituent (or substituents) relative to the above-named radicals is selected from the group consisting of amino, hydroxyl, cyano, carboxyl, nitro, chloro, bromo, fluoro, lower alkoxy having from 1 to 6 carbon atoms, mercapto, perhaloloweralkyl such astrifluoromethyl, loweralkylthio, guanidino, amidino, sulfamoyl, and N-substituted: sulfamoyl, amidino and guanidino wherein the N-substituent is loweralkyl having from 1 to 6 carbon atoms or aryl having 6–10 carbon atoms.

A particularly preferred class of compounds are those wherein $R^2$ is hydrogen, $R^3$ is selected from the group consisting of substituted and unsubstituted: loweralkyl having from 1 to 6 carbon atoms, cyclopropyl, benzyl and phenyl; and $R^1$ is an α-substituted alkyl wherein the α-substituent is hydroxyl, amino or mercapto and wherein the alkyl moiety is straight or branched and comprises 1 to 6 carbon atoms; the substituents relative to the above-named preferred radicals are selected from the group consisting of hydroxyl, bromo, fluoro, chloro, amino, amidino, guanidino, phenyl, mercapto, carboxyl, trifluoromethyl, loweralkylthio and loweralkoxyl wherein the alkyl moiety of the loweralkylthio and loweralkoxyl comprises 1 to 6 carbon atoms.

The preferred esters used as protecting groups are those where R' is benzyl, p-nitrobenzyl, o-nitrobenzyl, t-butyl, bromo-t-butyl, t-butyl-dimethylsilyl, trimethylsilyl, trichloroethyl; or R' represents pharmaceutically acceptable ester moieties such as pivaloyloxymethyl, allyl, methallyl, (2-methylthio)-ethyl, 3-methyl-2-butenyl, p-t-butylbenzyl, 5-indanyl, 3-phthalidyl.

Especially preferred embodiments of the present invention are those, as defined above, except that any unsubstituted amino group borne on radical $R^3$ of Structure I is derivatized according to the teachings of Belgium Pat. No. 848,545 (issued May 20, 1977); the resulting amino group being represented thusly (partial structure):

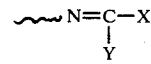

wherein X and Y are defined by the publication; species wherein X is H or lower alkyl and Y is $NH_2$ are especially preferred.

The products of this invention (I) form a wide variety of pharmacologically acceptable salts with inorganic and organic bases; these include, for example, metal salts derived from alkali metal or alkaline earth metal hydroxides, carbonates or bicarbonates and salts derived from primary, secondary or tertiary amines such as monoalkylamines, dialkylamines, trialkylamines, loweralkanolamines, di-loweralkanolamines, lower alkylenediamines, N,N-diaralkyl lower alkylenediamines, aralkylamines, amino substituted lower alkanols, N,N-di-loweralkylamino substituted lower alkanols, amino-, polyamino and guanidino-substituted lower alkanoic acids and nitrogen containing herocyclic amines. Representative examples include salts derived from sodium hydroxide, sodium carbonate, sodium bicarbonate, potassium carbonate, potassium hydroxide, calcium carbonate, trimethylamine, triethylamine, piperidine, morpholine, quinine, lysine, protamine, arginine, procaine, ethanolamine, morphine, benzylamine, ethylenediamine, N,N'-dibenzylethylenediamine, diethanolamine, piperazine, dimethylaminoethanol, 2-amino-2-methyl-1-propanol, theophylline, N-methylglucamine and the like.

Salts of the amino group carried in certain species of I on side chains $R^1$, $R^2$ and $R^3$ are also contemplated. Such pharmaceutically acceptable acid addition salts are derived from organic and inorganic acids such as HCl, HBr, citric, tartaric and the like.

The salts can be mono-salts such as the mono-sodium salt obtained by treating one equivalent of the product (I), also mixed di-salts. Such salts may be obtained by treating one equivalent of a base having a divalent cation, such as calcium hydroxide, with one equivalent of the product (I). The salts of this invention are pharmacologically acceptable nontoxic derivatives which can be used as the active ingredient in suitable unit dosage pharmaceutical forms. Also, they may be combined with other drugs to provide compositions having a broad spectrum of activity.

The novel 1-carba-2-penem-3-carboxylic acids of the present invention are valuable antimicrobial substances which are active against various gram-positive and gram-negative pathogens. Thus, the free acid and especially the salts thereof such as amine and metal salts, particularly the alkali metal and alkaline earth metal salts, are useful bactericides and can be used for removing susceptible pathogens from dental and medical equipment, for separating microorganisms, and for therapeutic use in humans and animals. For this latter purpose pharmacologically acceptable salts with inorganic and organic bases such as those known in the art and used for the administration of penicillins and cephalosporins can be utilized. For example, salts such as alkali metal and alkaline earth metal salts, and primary, secondary and tertiary amine salts can be used for this purpose. These salts can be combined with pharmaceutically acceptable liquid and solid vehicles to form suitable dosage unit forms such as pills, tablets, capsules, suppositories, syrups, elixirs and the like which can be prepared in accordance with procedures well known in this art.

The novel compounds are valuable antibiotics active against various gram-positive and gram-negative bacteria and, accordingly, find utility in human and veterinary medicine. The compounds of this invention can therefore be used as antibacterial drugs for treating infections caused by gram-positive or gram-negative bacteria, for example against *Staphylococcus aureus, Escherichia coli, Klebsiella penumoniae, Bacillus subtilis, Salmonella typhosa, Pseudomonas* and *Bacterium proteus.* The antibacterials of the invention may further be utilized as additives to animal feedingstuffs, for preserving foodstuffs and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in waterbased pains and in the white water of paper mills to inhibit the growth of harmful bacteria.

The products of this invention may be used alone or in combination as an active ingredient in any one of a variety of pharmaceutical preparations. These antibiotics and their corresponding salts may be employed in capsule form or as tablets, powders or liquid solutions or as suspension or elixirs. They may be administered orally, intravenously or intramuscularly.

Tablets and capsules for oral administration may be in unit dose presentation form, and may contain conventional excipients such as binding agents, for example, syrup, acacia, gelatin, sorbitol, tragacanth or polyvinylpyrrolidone; fillers for example, lactose, sugar, maize-starch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gleatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g., cocoa butter or other glyceride.

Compositions for injection may be presented in unit dose form in ampules, or in multidose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for reconstitution with a suitable vehicle, e.g., sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semisolid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition there may also be included in the composition other active ingredients to provide a broader spectrum of antibiotic activity.

For veterinary medicine the composition may, for example, be formulated as an intramammary preparation in either long acting or quick-release bases.

The dosage to be administered depends to a large extent upon the condition of the subject being treated and the weight of the host, the route and frequency of administration, the parenteral route being preferred for generalized infections and the oral route for intestinal infections. In general, a daily oral dosage consists of from about 15 to about 600 mg. of active ingredient per kg. of body weight of the subject in one or more applications per day. A preferred daily dosage for adult humans lies in the range of from about 80 to 120 mg of active ingredient per kg. of body weight.

The instant compositions may be administered in several unit dosage forms as, for example, in solid or liquid orally ingestible dosage form. The compositions per unit dosage, whether liquid or solid may contain from 0.5% to 99% of active material, the preferred range being from about 10-60%. The composition will generally contain from 15 mg. to about 1500 mg. of the active ingredient; however, in general, it is preferably to employ a dosage amount in the range of from about 250 mg. to 1000 mg. In parenteral administration the unit dosage is usually the pure compound in a slightly acidified sterile water solution or in the form of a soluble powder intended for solution.

The following examples illustrate but do not limit the product, process, compositional or method of treatment aspects of the present invention. All reaction temperatures are in °C.

EXAMPLE 1a

Preparation of Di-o-nitrobenzyltartarate

Tartaric acid (15.0 g, 0.1 mole) is dissolved in 40 ml. water and treated with lithium hydroxide (8.4 g, 0.2 mole). The resulting solution is evaporated to a small volume under reduced pressure and the residue is treated with p-dioxane. The resulting precipitate is filtered and dried under vacuum to give the di-lithium tartarate (17.7 g).

Di-lithium tartarate (9.46 g, 0.0585 mole) is suspended in 200 ml. DMF and treated with o-nitrobenzyl chloride (20 g, 0.117 mole) and sodium iodide (17.5 g, 0.117 mole). The mixture is stirred under $N_2$ for $2\frac{1}{2}$ days at 65° C.

The solvent is removed under vacuum and the resulting paste is treated with water and sodium thiosulfate (5 g). The resulting solid is filtered and dried to give di-o-nitrobenzyltartarate (17.0 g, 0.040 mole, 69%, m.p. 128° C.).

n.m.r. (DMSO): 4.8 d(j=7, H—C—OH), 5.23 d(j=7, H—C—OH), 5.7 S((O—CH₂—C₆H₄—NO₂); 7.73 & 8.2 m (aromatic H).

Similar treatment of the di-lithium salt with R'X (where X=Cl, Br or I) such as p-nitrobenzylbromide, benzylbromide, pivalyoxymethyl chloride gives the corresponding di-ester of tartaric acid such as di-p-nitrobenzyl tartarate, di-benzyl tartarate, dipivaloyloxymethyl tartarate. These can be used as equivalent alternates to di-o-nitrobenzyl tartarate in Example 2, below.

EXAMPLE 1

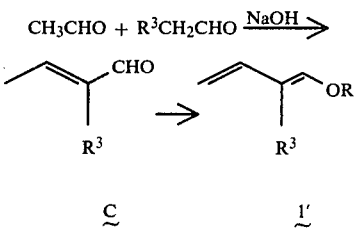

C          1'

The α,β-unsaturated aldehydes (C) are prepared by modified procedures reported by M. B. Green and W. J. Hickinbottom in J. Chem. Soc. 3262 (1957); and W. J. Bailey and R. Barclay Jr., J. Org. Chem., 21, 328 (1956).

Acetaldehyde (1 eq.) and propionaldehyde (R³=CH₃) (1 eq.) are placed in a three-necked round-bottom flask which is equipped with a mechanical stirrer, a dry-ice condenser, and a pressure equalized dropping-funnel. To the solution is added dropwise 1 eq. of 1 N NaOH through the dropping funnel with constant stirring. After completion of the mixing, the mixture is stirred for 10 min, then poured into a beaker containing crushed ice. Extraction of the mixture with ether gives the crude product. The desired product (C) is obtained by fractional distillation through a Widmer column.

Isopropenyl acetate (2 eq), cuprous acetate (0.002 eq) p-toluenesulfonic acid (0.008 eq.) and the α,β-unsaturated aldehyde C (1 eq.) are placed in a three-necked round-bottom flask equipped with a thermometer, a nitrogen inlet tube and a Widmer column which is attached with a distillation head. The mixture is heated at 93°-110° C. until quantitative acetone is collected. The mixture is then allowed to cool to r.t. and filtered from solids. The dark brown filtrate is mixed with triethanolamine in water at 0° C. The two layer mixture is distilled quickly under reduced pressure. The organic layer of the distillate is separated. The aqueous layer is extracted with 200 ml ether. The combined organic layer is washed with 10% K₂CO₃, dried over Na₂SO₄, and evaporated in vacuo. The residue so obtained is mixed with 2.0 g N-phenyl-β-naphthamine and distilled under reduced pressure to give the desired 2-substituted 1-acetoxy-1,3-butadiene (1').

Following the procedure of Example 1, the following R³ substituted species are obtained. (Table I).

TABLE I

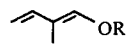

|    | R³ | R |
|----|----|----|
| 1. | CH₃ | CH₃C(=O)— |
| 2. | CH₃CH₂ | CH₃C(=O)— |
| 3. | CH₃CH₂CH₂ | CH₃C(=O)— |
| 4. | (CH₃)₂CH | CH₃C(=O)— |
| 5. | cyclopropyl | CH₃C(=O)— |
| 6. | Ph (Ph=phenyl) | CH₃C(=O)— |
| 7. | PhCH₂ | CH₃C(=O)— |

EXAMPLE 2

Preparation of 6-(1-hydroxyethyl)-1-methyl-2-(p-aminomethylphenyl)-1-carbadethiapen-2-em-3-carboxylic acid

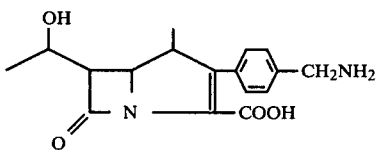

Step A

Preparation of 1'

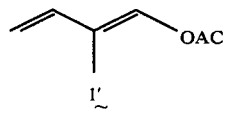

1'

Isopropenyl acetate (182 g), cupric acetate (0.40 g), 2-methyl-2-butenal (84 g) and p-toluenesulfonic acid (1.52 g) are placed in a 1.0-1, three-necked flask equipped with a thermometer, a nitrogen inlet tube and a 10-in. Widmer column which is attached with a distillation head. The mixture is heated at 93°-110° C. until 73 ml of acetone is collected. After cooling to r.t. (25° C.) the mixture is filtered from solids. The dark brown filtrate is cooled in an ice-bath and mixed with 3.4 g triethanolamine in 200 ml water. The two layer mixture is distilled quickly at 53 mm (b.p. 54° C.). The organic layer of the distillate is separated. The aqueous layer is extracted with 200 ml ether. The organic layers are combined and washed with 10% K₂CO₃, dried over Na₂SO₄, and evaporated in vacuo. The residue so obtained is mixed with 2.0 g N-phenyl-β-naphthamine and distilled under reduced pressure to give 1' (97 g), b.p. 81°-91° (66 mm).

Step B

Preparation of 2' and 3'

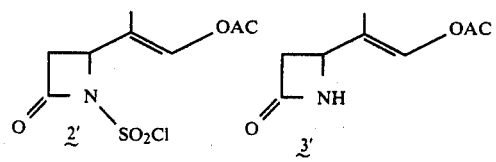

Chlorosulfonylisocyanate (CSI) (6.5 ml) is placed in a three-necked, 100-ml flask equipped with a thermometer, a magnetic stirring bar a nitrogen inlet tube and a 25-ml pressure-equalized dropping funnel. The CSI is chilled to −50° C. and mixed with 12.5 ml ether through the dropping funnel. The etheral solution of CSI is allowed to warm up to −25° C., to the solution is added dropwise 1-acetoxyl-2-methyl-1,3-butadiene (1') (5.9 ml in 12.5 ml ether) in 30 min. The mixture is then stirred for 20 min at −20°+3° C. The white precipitate formed initially is redissolved at the end of the reaction.

In a 500-ml round bottom flask, a solution of 10 g sodium sulfite and 25 g potassium hydrogen phosphate in 100 ml water is prepared and is cooled in an ice bath. Ether (100 ml) and crushed ice (100 g) are added and the mixture is vigorously stirred in an ice bath. At the end of 20 minutes reaction time, the reaction mixture which contains 2' is transferred into the dropping funnel and added dropwise to the hydrolysis mixture in 5 minutes. The hydrolysis is allowed to continue for an additional 30 minutes at 3° C. The organic layer is separated and the aqueous is extracted with 50 ml ether. The organic layers are combined, dried over $Na_2SO_4$ and evaporated to give crystalline product 3' (2.3 g), m.p. 77°–78,5°; m.s. 169 (M+); IR 1760 $cm^{-1}$ (β-lactam); NMR (300 MHz, CDCl$_3$): 1.70 (d), 2.16 (s), 2.84 (qq), 3.18 (qq), 4.20 (m), 5.82 (broad, and 6.26 (s) ppm.

Step C

Preparation of 4':

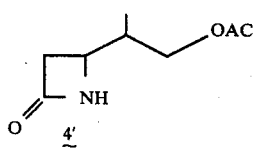

4-(1-methyl-2-acetoxyvinyl)azetidine-2-one (3') (6.5 g) is hydrogenated on a Parr shaker at r.t. under 40 psi hydrogen in the presence of 10% Pc/C (0.6 g) in 200 ml ethylacetate for 2 hr. The mixture is filtered from the catalyst and the filtrate is evaporated in vacuo to give the crude product. Purification of the crude product by high pressure liquid chromatograph (HPLC) (silical gel column, 30% ethylacetate/CH$_2$Cl$_2$ solvent system) affords white crystalline product 4' (6.04 g) after evaporation of solvent. The product shows following physical characteristics: ms 171 (M+); IR (Neat) 1754 $cm^{-1}$; NMR (60 MHz, CDCl$_3$): 0.96 (d), 1.01 (d), 2.06 (d, OAc), 2.75–3.80 (m), 3.99 (d) and 6.80 (broad) ppm.

STEP D

Preparation of 5'

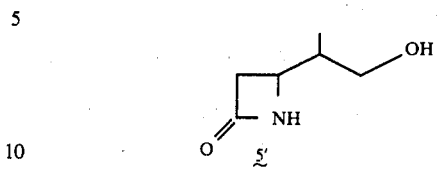

Under N$_2$ at 0°, a solution of 4-(1-methyl-2-acetoxyethyl)-2-azetidinone 4' (1.2 g) in 10 ml methanol is treated with sodium methoxide (57 mg). After stirring for 1 hr, the solution is neutralized with glacial acetic acid (65 mg). Removal of methanol in vacuo gives crude 4-(1-methyl-2-hydroxyethyl)-2-azetidinone (5') as an oil. The product is purified and chromatography on silica gel eluting with ethyl acetate to give 0.78 g of 5':

IR (neat): 1740 $cm^{-1}$; NMR (CDCl$_3$): 0.77 (d), 0.96 (d), 1.90 (m), 2.60–3.30 (m), 3.60 (m), 4.19 (s), and 7.23 (s). The product crystallizes as colorless solids in the refrigerator.

STEP E

Preparation of 6'

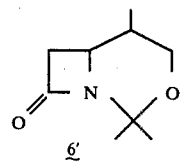

A solution of 4-(1-methyl-2-hydroxyethyl)-2-azetidinone (0.5 g) and 2,2-dimethoxypropane (0.48 g) in 10 ml anhydrous methylene chloride is treated with boron trifluoride (55 mg) at room temperature for 90 min. The mixture is washed with 5 ml saturated NaHCO$_3$. The organic layer is separated, dried over Na$_2$SO$_4$ and allowed to evaporate in vacuo to give crude isomeric mixture of 6' (0.48 g) as an oil.

Separation of isomers 6'α and 6'β is accomplished by high pressure liquid chromatograph (HPLC) (silica gel) eluting with 40% ethylacetate/hexanes. After evaporation of the solvents affords 150 mg of 6'β as an oil and 200 mg of 6'α as a white solid.

NMR (300 MHz, CDCl$_3$) of 6'α: 0.81 (d), 1.31 (s), 1.68 (s), 1.62 (m), 2.52 (g), 3.05 (m), 3.42 (t), and 3.66 ppm (q), NMR (300 MHz, CDCl$_3$) of 6'β: 1.10 (d), 1.38 (s), 1.67 (s), 1.90 (m), 2.80 (q), 2.86 (q), 3.62 (q), 3.78 (m) and 3.98 (q) ppm.

STEP Fa

Preparation of 7'α

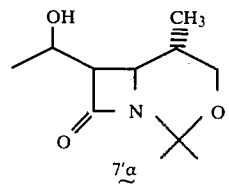

At −78° C., diisopropylamine (2.2 g) in 20 ml of anhydrous tetrahydrofuran is treated with n-butyllithium (1.6 M in n-hexane, 14 ml) for 5 min. To the solution is added 8-oxo-5α, 2,2-trimethyl-1-azabicyclo[4.2.0]octane (6'α) (3.4 g) and the mixture is stirred for 10 min. The resulting lithium enolate is treated with acetaldehyde (1.68 ml). The mixture is stirred for 1 min. then is quenched with 24 ml saturated ammonium chloride at −78° C., then allowed to warm to room temperature (25° C.). The mixture is extracted with ethylacetate (2×100 ml). The organic layer is separated, dried over Na₂SO₄ and allowed to evaporate in vacuo to give 4.5 g of the crude product 7'α.

The crude isomeric mixture of 7'α is purified and separated by HPLC (silica gel) eluting with 50% ethylacetate/methylene chloride to give 3.5 g of trans-7'α and 0.5 g of cis-7'α. Both isomers are crystalline solids.

STEP Fb

Preparation of 7'β

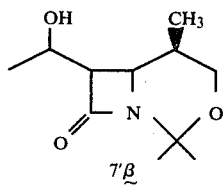

Following the procedure of Step Fa, except replacing the starting material 6'α with 6'β isomer, the products, trans-7'β (4.0 g) and cis-7'β (0.1 g), are obtained.

STEP Fc

Preparation of 7''β

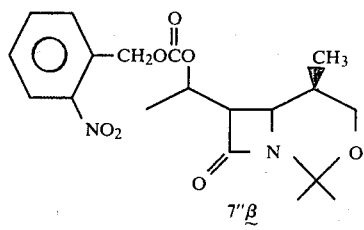

Under anhydrous conditions at 0° C. a solution of R enriched trans-7'β (2.90 g) in 60 ml methylene chloride is treated with 4-dimethylaminopyridine (3.32 g) and o-nitrobenzylchloroformate (5.88 g). The mixture is allowed to warm to room temperature and stirred for 1 hr. The resulting mixture is washed with 0.1 N HCl, water, brine and water. The organic layer is separated, dried over Na₂SO₄ and allowed to evaporate in vacuo to give crude products. The crude products dissolved in 20 ml ether and chilled at −5° C. gives the o-nitrobenzyl alcohol (0.5 g) which is separated by filtration. The isomeric mixture trans-7''β is purified and separated by HPLC (silica gel) eluting with 40% ethylacetate/cyclohexane to give 1.2 g of S-trans-7''β and 1.0 g of R-trans-7''β.

The spectra data of R-trans-7''β: NMR (300 MHz, CDCl₃): 1.12 (d), 1.40 (s), 1.46 (d), 1.73 (s), 1.95 (m), 3.20 (q), 3.60 (q), 3.74 (q), 3.95 (q), 5.07 (m), 5.58 (q), 7.56 (t), 7.70 (m) and 8.19 (d)ppm.

The spectra data of S-trans-7''β: NMR (300 MHZ, CDCl₃): 1.10 (d), 1.40 (s), 1.43 (d), 1.72 (s), 1.94 (m), 3.34 (q), 3.61 (q), 3.67 (q), 3.96 (q), 5.13 (m), 5.64 (d), 7.53 (m), 7.68 (m), and 8.17 (d)ppm.

STEP Fd

Preparation of 7''α

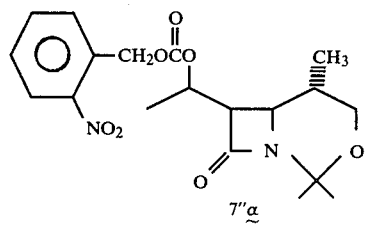

Following the procedure of Step Fc; except replacing the starting material trans-7'β with trans-7'α isomer, the products R-trans-7''α and S-trans-7''α are obtained. The following chart summarizes the foregoing separation:

TABLE II
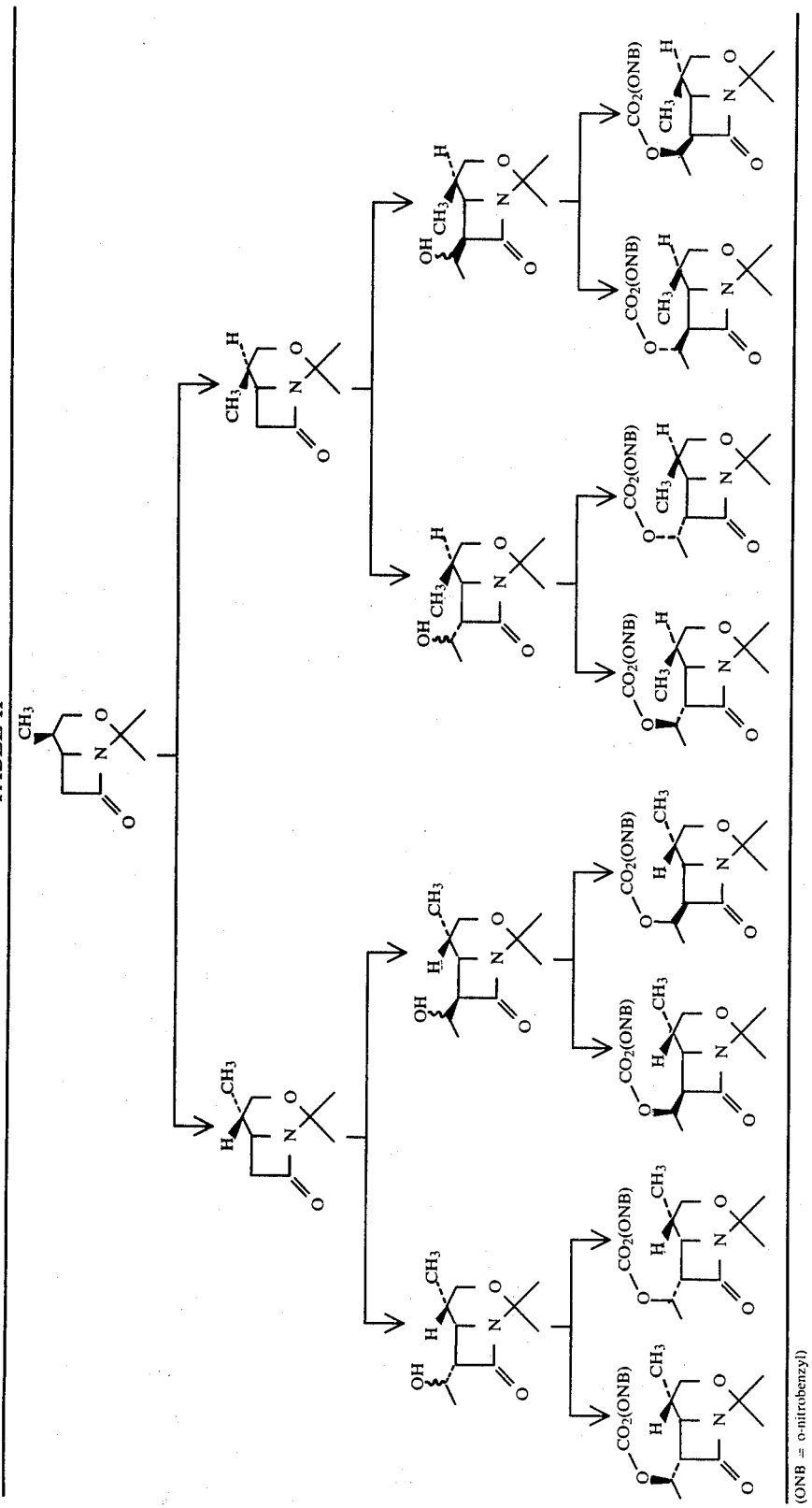
(ONB = o-nitrobenzyl)

STEP Ga

Preparation of R-trans-9'β:

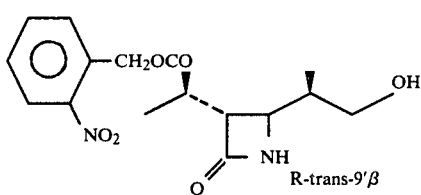

8-Oxo-3-oxa-5β-2,2-trimethyl-7α-(1R-o-nitrobenzyl-carbonyldioxyethyl)-1-azabicyclo[4.2.0]octane (R-trans-7"β) (2.1 g) is dissolved in 4 ml trifluoroacetic acid and 4 ml water at room temperature and the mixture is stirred for 10 minutes. The resulting homogeneous solution is slowly poured into a vigorously stirred saturated solution of potassium bicarbonate (30 ml) in a 200-ml beaker. The mixture is extracted with methylene chloride (200 ml). The organic layer is separated, dried over Na₂SO₄ and allowed to evaporate in vacuo to give crude product 9' which is purified by a silica gel column eluting with 40% ethylacetate/cyclohexane to afford product R-trans-9'β as an oil NMR (300 MHz, CDCl₃): 0.98 (d), 1.28 (d), 2.85 (m), 3.20 (q), 3.62 (m), 5.12 (m), 5.57 (q), 6.40 (s), 7.53 (t), 7.66 (m) and 8.14 (d).

Step Gb

Following the procedure of Step Ga, except systematically replacing the starting material with the other isomers, the other isomeric products are obtained (Table III).

TABLE III

| Starting material | Product |
|---|---|
| S-trans-7"β | S-trans-9'β |
| R-trans-7"α | R-trans-9'α |
| S-trans-7"α | S-trans-9'α |
| R-cis-7"α | R-cis-9'α |
| S-cis-7"α | S-cis-9'α |
| R-cis-7"β | R-cis-9'β |
| S-cis-7"β | S-cis-9'β |

STEP Ha

Preparation of R-trans-1β:

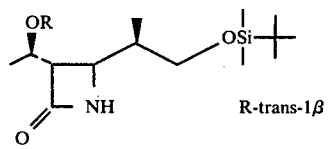

The starting material R-trans-9'β (1.58 g, 4.5 mmol) is treated with 5 equivalents of t-butyldimethylchlorosilane, 10 equivalents of imidazole in 5 ml anhydrous N,N-dimethylformamide (DMF) at room temperature for 3 hrs. The mixture is allowed to evaporate in vacuo to give crude product. Purification of the crude product by a silica gel column eluting with 30% ethylacetate/cyclohexane gives 2.0 g of the product (R-trans-1β), NMR (300 MHz, CDCl₃): 0.04 (s), 0.88 (s), 0.98 (d), 1.26 (d), 1.82 (m), 3.20 (q), 3.60 (m), 5.15 (m), 5.59 (q), 5.94 (s), 7.54 (t), 7.68 (m) and 8.18 (d)ppm.

STEP Hb

Following the procedure of Step Ha, except replacing the starting material, the other isomeric products are obtained (Table IV).

TABLE IV

| Starting Material | Product |
|---|---|
| S-trans-9'β | S-trans-1β |
| R-trans-9'α | R-trans-1α |

TABLE IV-continued

| Starting Material | Product |
|---|---|
| S-trans-9'α | S-trans-1α |
| R-cis-9'α | R-cis-1α |
| S-cis-9'α | S-cis-1α |
| R-cis-9'β | R-cis-1β |
| S-cis-9'β | S-cis-1β |

STEP I

Preparation of 2

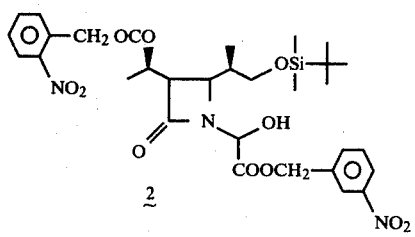

2 o-Nitrobenzyl-d-tartarate (1.8 g) is oxidized with periodic acid (0.97 g) in 18 ml of anhydrous tetrahydrofuran at 25° C. for 30 min. The mixture is filtered from solids and the filtrate is allowed to evaporate in vacuo to give o-nitrobenzylglyoxylate which is then taken up in 100 ml benzene and transferred into a 250-ml round bottom flask. To the solution is added trans-3-[1(R)-o-nitrobenzyloxycarbonyloxyethyl]-4-[1β-methyl-2-t-butyldimethylsilyloxy)ethyl]-2-azetidinone (R-trans-1β) (2.0 g). The mixture is heated at reflux and water removed with a Dean-Stark trap packed with CaH₂ (1 g). for 6 hr. The mixture is cooled, filtered, evaporated and chromatographed on silica gel eluting with 30% ethylacetate/cyclohexane to give 2.

STEP J

Preparation of 3 and 4

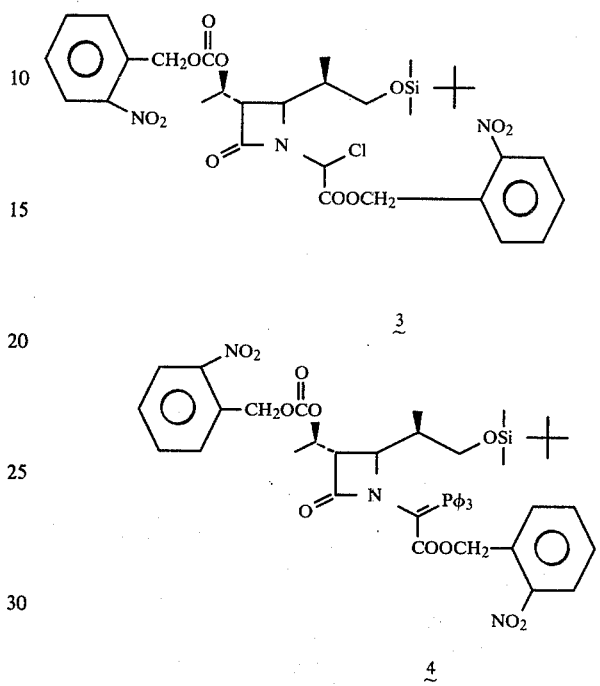

Trans-1-(o-nitrobenzyloxycarbonylhydroxymethyl)-3-[1(R)-o-nitrobenzyloxycarbonyloxyethyl]-4-[(1β-methyl-2-t-butyldimethylsilyloxy)ethyl]-2-azetidinone (2) (3.92 g) in 20 ml anhydrous tetrahydrofuran at −20° C. is treated with pyridine (0.42 ml) and thionyl chloride (0.37 ml). The mixture is allowed to warm to 25° C. with stirring, then filtered from solids. After removal of solvent in vacuo, product 3 is obtained. The chloride 3 is redissolved in 25 ml anhydrous DMF and treated with triphenylphosphine (1.1 g) with stirring at 25° C. for 1 hr. Solvent is removed in vacuo and the residue is dissolved in 100 ml methylene chloride and washed with 0.1 N pH 7.2 phosphate buffer 30 ml; chromatographic purification on silica gel eluting with 40% ethylacetate/cyclohexane, gives product 4 (1.0 g).

STEP K

Preparation of 5

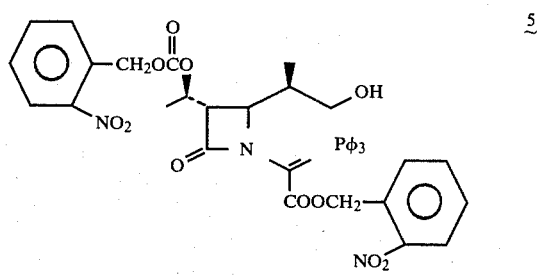

Trans-1-(o-nitrobenzyloxycarbonyltriphenylphosphoranylmethyl)-3-[1(R)-o-nitrobenzyloxycarbonyloxyethyl]-4-[1β-methyl-2-t-butyldimethylsilyloxy)ethyl]-

2-azetidinone (4) (1.0 g) is dissolved in 10 ml tetrahydrofuran and is treated with conc. HCl (0.41 ml) at 25° C. for 10 min. The mixture is diluted with 200 ml methylene chloride then washed with 0.1 M Na₂HPO₄ (50 ml) The organic layer is separated, dried over Na₂SO₄ and evaporated in vacuo to give crude 5. Chromatographic pruification of the crude product eluting with 30% ethylacetate/cyclohexane gives 0.68 g of 5.

Step L

Preparation of 6:

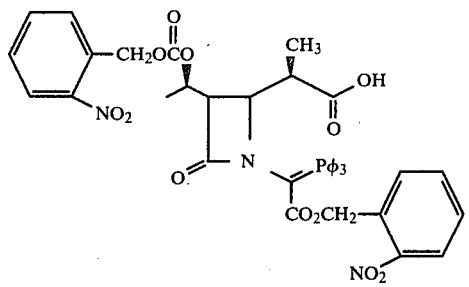

One gram of 1-(o-nitrobenzyloxycarbonylmethyltriphenylphosphoranyl)-4-(1-methyl-2-hydroxyethyl)-6-(o-nitrobenzyloxycarbonyloxyethyl)-2-azetidinone is dissolved in 20 ml. acetone and cooled to 0° C. Jones Reagent (1 ml., 4 N solution) is added dropwise over 5 min and the resulting solution is stirred at 0° C. for 10 min. Isopropanol (0.1 ml) is added. The mixture is stirred for another 2 min. The reaction mixture is diluted with CH₂Cl₂ and filtered. The filtrate is washed with saturated NaCl solution, dried and evaporated to give crude acid which is used without further purification in the next step.

Step M

Preparation of 7 and 8

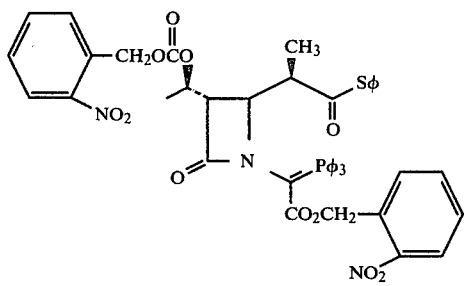

1-(o-nitrobenzyloxycarbonylmethyltriphenylphosphoranyl)-4-(1-methyl-2-carboxymethyl)-6-(1-o-nitrobenzyloxycarbonyloxyethyl)-2-azetidinone (0.851 g) is dissolved in 20 ml CH₂Cl₂ and cooled to 0° C. under N₂. Oxalyl chloride (0.8 ml) is added dropwise over 5 min and then 1 drop of DMF is added. The mixture is stirred at 0° C. for 5 min and then at 25° C. for 15 min. The solvent and excess oxalyl chloride are evaporated under reduced pressure. The residue is the desired acid chloride 7. The acid chloride is dissolved in 20 ml CH₂Cl₂ and cooled to 0°, under N₂. Thiophenol (0.4 g) is added and then pyridine 0.8 ml is added dropwise. The reaction mixture is stirred at 0° C. for 5 min, then at 25° C. for 15 min, then diluted with CH₂Cl₂ and washed with water, dried and evaporated. The residue is chromatographed on silica gel using 50% EtOAc/C₆H₅ as eluant, to give the thio ester.

Step N

Preparation of 9a

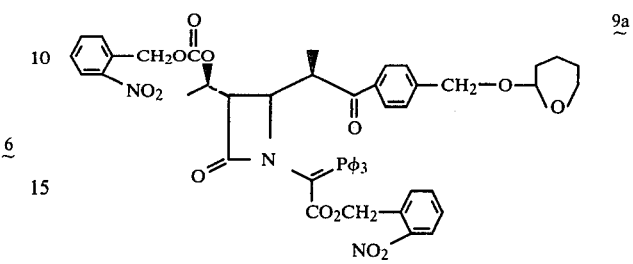

Cuprous iodide (0.380 g) is suspended in 10 ml anhydrous ether under N₂, in a dry flask and cooled to 0°. p-Tetrahydropyranyloxymethylphenylmagnesiumbromide (prepared from p-tetrahydropyranyloxymethylphenylbromide with magnesium in THF) (3.0 ml, 1.3 Molar) is added dropwise and the mixture is stirred at 0° for 5 min to give a yellow suspension. The mixture is then cooled to −50°. 1-(p-nitrobenzyloxycarbonyl-triphenylphosphoranylmethyl)-4-(methylphenylthiocarbonylmethyl)-2-azetidinone (0.674 g) in 10 ml THF is added dropwise over 5 min. The mixture is stirred at −50° for 5 min and allowed to come to −20° over 20 min and stirred at −20° for 5 min. Saturated NH₄Cl solution 5 ml is added and the mixture is diluted with CH₂Cl₂. Stirred at r.t. for 5 min. The organic phase is separated, dried and evaporated. The residue is chromatographed on silica gel using EtOAc as eluant to give the product.

Step O

Preparation of 9b

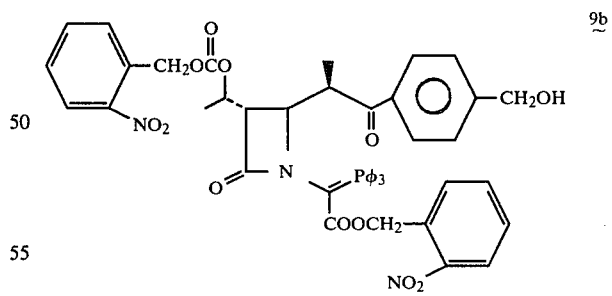

The THP ether (0.42 g) obtained from Step N is dissolved in 4 ml acetic acid and 1 ml of 10% sulfuric acid. The mixture is stirred at 25° C. for 0.5 hr. Then the mixture is poured slowly into a beaker containing 20 ml saturated KHCO₃. The mixture is extracted with methylene chloride. The organic layer is separated, dried over MgSO₄, and allowed to evaporate in vacuo. The residue is chromatographed on TLC plates to give the desired alcohol.

Step P

Preparation of 9c

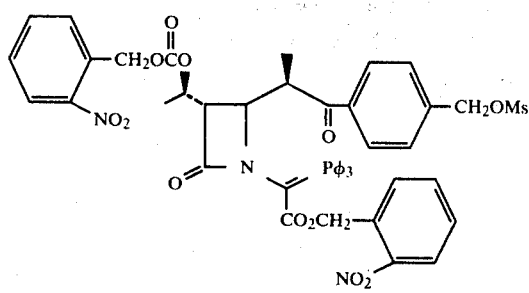

The alcohol (90 mg) is dissolved in 5 ml CH₂Cl₂ and treated with 34 μl of methanesulfonyl chloride and 42 μl of triethylamine at 0° C., and stirred for 0.5 hr. The mixture is diluted with methylene chloride and washed with water. The organic layer is separated, dried over MgSO₄ and allowed to evaporate in vacuo. The residue is chromatographed on TLC to give the desired product.

Step Q

Preparation of 9d

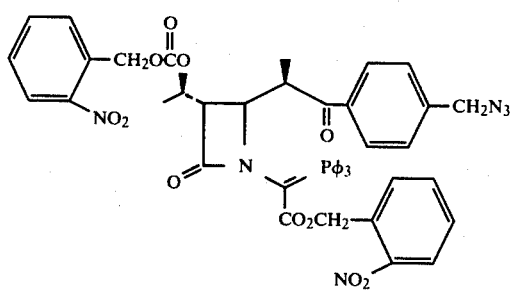

The mesylate ylide (72 mg) is treated with lithium azide in DMF at 25° C. overnight. The mixture is allowed to evaporate in vacuo. The residue chromatographed on TLC (silica gel) gives the desired product.

Step R

Preparation of 10:

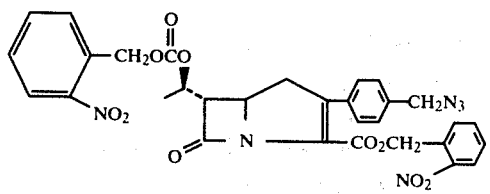

The azido ylide (61 mg) is dissolved in 3 ml xylene and heated at 140° under N₂ for 1.5 hr. The mixture is cooled to 25° C. Xylene is removed under reduced pressure. The residue chromatographed on a silica gel plates gives the desired product.

Step S

Preparation of I:

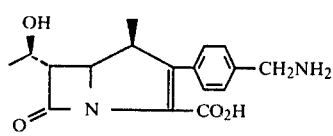

The carbapenem (10 mg) ester is dissolved in 1 ml dioxane. To the solution is added 1 ml water and 0.2 ml ethanol. The solution is adjusted to pH 3.5 with diluted HCl. One mg of 10% Pd/C is added. The mixture is hydrogenated for 20 min at 40 psi.

The mixture is filtered from catalyst, and the filtrate is extracted with 3×5 ml ether. The aqueous layer is separated and chromatographed on an XAD-2 column eluted with water to give the title compound (I).

EXAMPLE 3

Preparation of 6-(hydroxymethyl)-1,6-dimethyl-2-(2-aminoethyl)-1-carbadethiapen-2-em-3-carboxylic acid

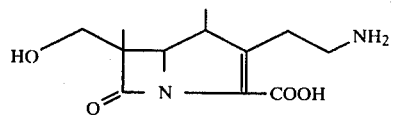

Step A:

Preparation of 11

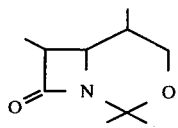

THF, 20 ml is placed under N₂, treated with 1.54 ml diisopropylamine and cooled to 078° C. A solution of n-butyl lithium 197 M in hexane 5.6 ml is added dropwise over 5 min. The reaction mixture is stirred at −78° C. for 10 min and then treated with 9-oxo-2,2,5,-trimethyl-3-oxa-1-azabicyclo[4.2.0]octane (1.55 g) in 15 ml THF added dropwise over 5 min. After another 10 min hexamethylphosphoramide 1.97 ml is added. The mixture is stirred another 10 min, then treated with 2 ml of methyl iodide. The reaction mixture is stirred at −78° C. for 15 min and allowed to warm to 25° C. and stirred for 15 min. The reaction mixture is diluted with EtOAc, washed once with pH 7 phosphate buffer then dried and evaporated. The residue is chromatographed on silic gel using 25% EtOAc/C₆H₆ as eluant to give 8-oxo-2,2,5,7-tetramethyl-3-oxa-1-azabicyclo[4.2.0]octane.

Step B

Preparation of 12

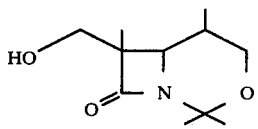

To a solution of 1.1 equivalents of freshly prepared lithium diisopropylamide in anhydrous tetrahydrofuran under a nitrogen atmosphere at −78° is added a solution of 8-oxo-2,2,5,7-tetramethyl-3-oxa-1-azabicyclo-[4.2.0]octane in anhydrous tetrahydrofuran which has been cooled to −78° C. After two minutes, the resulting lithium enolate is treated with excess formaldehyde, introduced as a gas just above the surface of the stirred solution. The solution is stirred for 30 minutes at −78° and then poured into water. The aqueous phase is saturated with sodium chloride and extracted with ethyl acetate. The combined ethyl acetate solutions are dried over magnesium sulfate and filtered. The filtrate is evaporated under reduced pressure to give the crude product. Purification by chromatographed on silica gel using ethyl acetate/benzene gives 8-oxo-2,2,5,7-tetramethyl-7-(hydroxymethyl)-3-oxa-1-azabicyclo[4.2.0]octane.

Step C

Preparation of 13

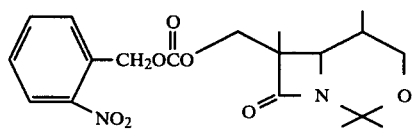

Under anhydrous conditions at 0° C. a solution of 8-oxo-2,2,5,7-tetramethyl-7-(hydroxymethyl)-3-oxa-1-azabicyclo[4.2.0]octane (60 mg) in 0.6 ml ether is treated with powdered potassium hydroxide (19mg). After a period of 15 minutes, p-nitrobenzyl chloroformate (65 mg) is added to the reaction mixture. Stirring is continued at 25° C. for an additional 15 hours. The mixture is partitioned between 1 M pH 7 phosphate buffer and more ether. The ether phase is washed with water and brine, dried over magnesium sulfate and filtered. Evaporation of the filtrate under reduced pressure gives 67 mg of a colorless oil. Purification by preparative thick-layer chromatography on silica gel developing with 1:9 ethylacetate/benzene gives 8-oxo-2,2,5,7-tetramethyl-7-(p-nitrobenzylcarbonyldioxymethyl)-3-oxa-1-azabicyclo-[4.2.0]octane as a mixture of diastereomers.

Step D

Preparation of 14

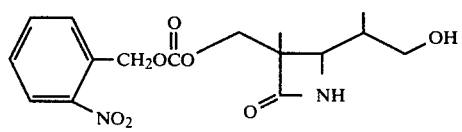

8-Oxo-3-oxa-2,2,5,7-tetramethyl-7-(1-o-nitrobenzylcarbonyldioxymethyl)-1-azabicyclo[4.2.0]octane (1.0 g) is dissolved in 8 ml acetic acid and 2 ml water and heated at 65° C. for 1.25 hours. The acetic acid and water are removed under reduced pressure and the residue is taken up in benzene and evaporated to give 3-methyl-3-(o-nitrobenzylcarbonyldioxymethyl)-4-(1-methyl-2-hydroxyethyl)-2-azetidinone as a mixture of diastereoisomers.

STEP E

Preparation of 15

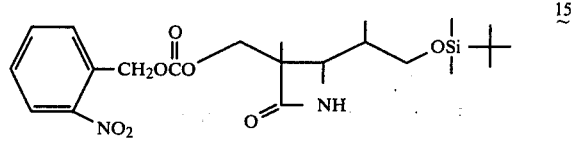

The starting material 14 (1.58 g, 4.5 mmol) is treated with 5 equivalents of t-butyldimethylchlorosilane, 10 equivalents of imidazole in 5 ml anhydrous N,N-dimethylformamide (DMF) at room temperature for 3 hrs. The mixture is allowed to evaporate in vacuo to give crude product. Purification of the crude product by a silica gel eluting with 30% ethylacetate/cyclohexane gives the product 15.

STEP F

Preparation of 16:

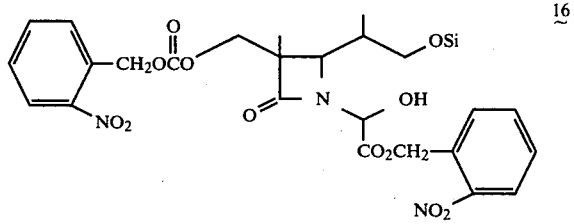

o-Nitrobenzyl-d-tartarate (1.8 g) is oxidized with periodic acid (0.97 g) in 18 ml of anhydrous tetrahydrofuran at 25° C. for 30 min. The mixture is filtered from solids and the filtrate is allowed to evaporate in vacuo to give o-nitrobenzylglyoxylate which is then taken up in 100 ml benzene and transferred into a 250-ml round bottom flask. To the solution is added [3-methyl-o-nitrobenzyloxycarbonyloxymethyl]-4-[1β-methyl-2-t-butyldimethylsilyoxy)ethyl]-2-azetidinone (2.0 g). The mixture is heated at reflux and azeotropically removal of water with a Dean-Stark trap packed with CaH$_2$ (1 g). for 6 hr. The mixture is cooled, filtered, evaporated and chromatographed on silica gel eluting with 30% ethylacetate/cyclohexane to give 2.

STEP Fa

Preparation of 17 and 18

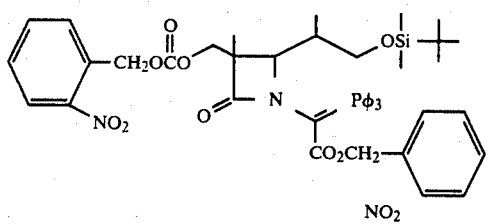

The starting material 16 (3.92 g) in 20 ml anhydrous tetrahydrofuran at −20° C. is treated with pyridine (0.42 ml) and thionyl chloride (0.37 ml). The mixture is allowed to warm to 25° C. with stirring, then filtered from solids. After removal of solvent in vacuo, product 17 is obtained. The chloride 17 is redissolved in 25 ml anhydrous DMF and treated with triphenylphosphine (1.1 g) with stirring at 25° C. for 1 hr. Solvent is removed in vacuo and the residue is dissolved in 100 ml methylene chloride and washed with 0.1 N pH 7.2 phosphate buffer 30 ml, chromatographic purification on silica gel eluting with 40% ethylacetate/cyclohexane gives product 18 (1.0 g).

STEP G

Preparation of 18

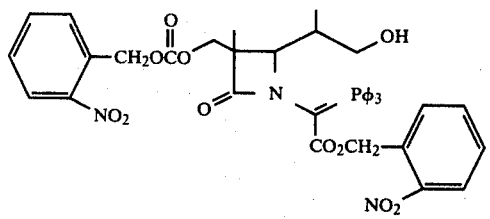

The starting material 17 (1.0 g) is dissolved in 10 ml tetrahydrofuran and is treated with conc. HCl (0.41 ml) at 25° C. for 10 min. The mixture is diluted with 200 ml methylene chloride then washed with 0.1 M $Na_2HPO_4$ (50 ml) The organic layer is separated, dried over $Na_2SO_4$ and evaporated in vacuo to give crude 18. Chromatographic pruification of the crude product eluting with 30% ethylacetate/cyclohexane gives 0.68 g of 18.

STEP H

Preparation of 19

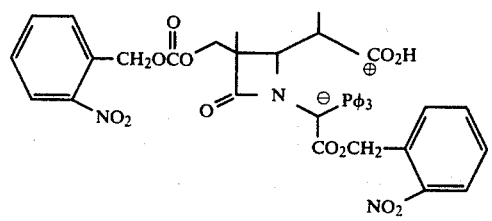

One gram of 1-(o-nitrobenzyloxycarbonylmethyltriphenylphosphoranyl)-4-(1-methyl-2-hydroxyethyl)-3-methyl-3-(o-nitrobenzyloxycarbonyloxymethyl)-2-azetidinone is dissolved in 20 ml. acetone and cooled to 0° C. Jones Reagent (1 ml., 4 N solution) is added dropwise over 5 min and the resulting solution is stirred at 0° C. for 10 min. Isopropanol (0.1 ml) is added. The mixture is stirred for another 2 min. The reaction mixture is diluted with $CH_2Cl_2$ and filtered. The filtrate is washed with saturated NaCl solution, dried and evaporated to give 0.851 g of crude acid 19 which is used without further purification in the next step.

STEP I

Preparation of 20

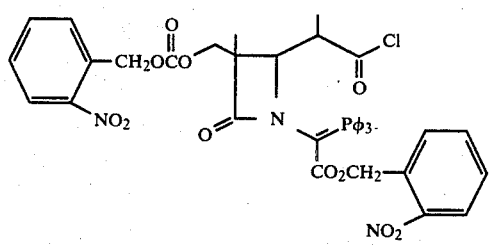

From Step H, 1-(o-nitrobenzyloxycarbonylmethyltriphenylphosphoranyl)-4-(1-methyl-2-carboxymethyl)-3-methyl-3-(o-nitrobenzyloxycarbonyloxymethyl)-2-azetidinone (0.851 g) is dissolved in 20 ml $CH_2Cl_2$ and cooled to 0° C. under $N_2$. Oxalyl chloride (0.8 ml) is added dropwise over 5 min. and then 1 drop of DMF is added. The mixture is stirred at 0° C. for 5 min and then at 25° C. for 15 min. The solvent and excess oxalyl chloride are evaporated under reduced pressure. The residue is the desired acid chloride which is used without purification in the next step.

Step J

Preparation of 21

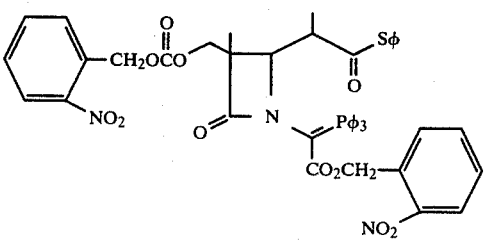

The product from Step I is dissolved in 20 ml $CH_2Cl_2$ and cooled to 0°, under $N_2$. Thiophenol (0.4 g) is added and then pyridine 0.8 ml is added dropwise. The reaction mixture is stirred at 0° for 5 min, then at 25° C. for 15 min, then diluted with $CH_2Cl_2$ and washed with water, dried and evaporated. The residue is chromatographed on silic gel using 50% $EtOAc/C_6H_5$ as eluant, to give the thio ester.

STEP K

Preparation of 22

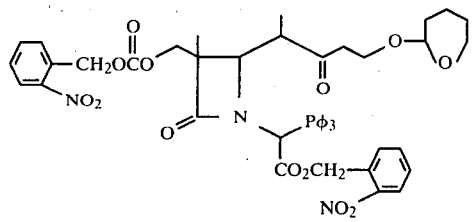

Cuprous iodide (0.380 g) is suspended in 10 ml anhydrous ether under N₂, in a dry flask and cooled to 0°. THP-OCH₂CH₂MgBr (3.0 ml, 1.3 Molar) is added dropwise and the mixture is stirred at 0° for 5 min. The mixture is then cooled to −50°. Compound 21, (0.674 g) in 10 ml THF is added dropwise over 5 min. The mixture is stirred at −50° for 5 min and allowed to come to −20° over 20 min and stirred at −20° for 5 min. Saturated NH₄Cl solution 5 ml is added and the mixture is diluted with CH₂Cl₂. Stirred at r.t. for 5 min. The organic phase is separated, dried and evaporated. The residue is chromatographed on silica gel using EtOAc as eluant to give the product.

Step L

Preparation of 23

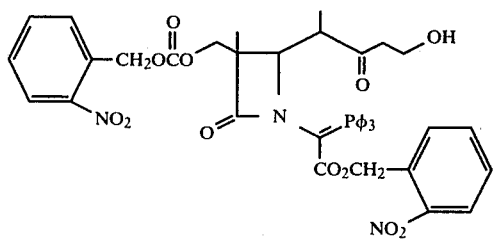

The THP ether (0.42 g) obtained from Step N is dissolved in 4 ml acetic acid and 1 ml of 10% sulfuric acid. The mixture is stirred at 25° C. for 0.5 hr. Then the mixture is poured slowly into a beaker containing 20 ml saturated KHCO₃. The mixture is extracted with methylene chloride. The organic layer is separated, dried over MgSO₄, and allowed to evaporate in vacuo. The residue is chromatographed on TLC plates to give the desired alcohol.

Step M

Preparation of 24

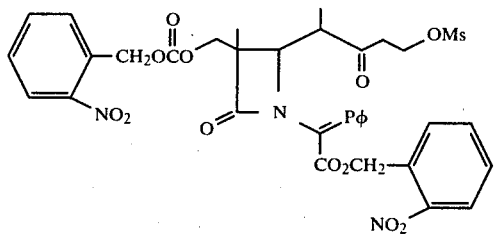

The alcohol (90 mg) is dissolved in 5 ml CH₂Cl₂ and treated with 34 μl of methanesulfonyl chloride and 42 μl of triethylamine at 0° C., and stirred for 0.5 hr. The mixture is diluted with methylene chloride and washed with water. The organic layer is separated, dried over MgSO₄ and allowed to evaporate in vacuo. The residue is chromatographed on TLC to give the desired product.

Step N

Preparation of 25

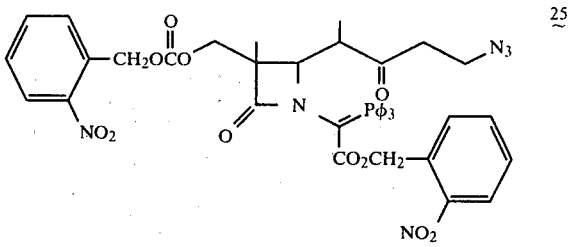

The mesylate ylide (72 mg) is treated with lithium azide in DMF at 25° C. overnight. The mixture is allowed to evaporate in vacuo. The residue chromatographed on TLC (silica gel) gives the desired product.

Step O

Preparation of 26

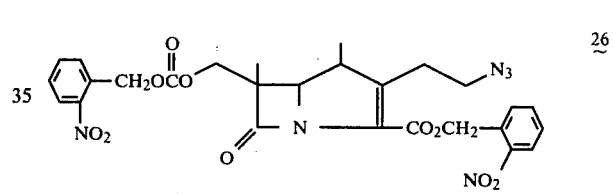

The azido ylide (61 mg) is dissolved in 3 ml xylene and heated at 140° under N₂ for 1.5 hr. The mixture is cooled to 25° C. Xylene is removed under reduced pressure. The residue chromatographed on a silica gel plates gives the desired product.

Step P

Preparation of 27

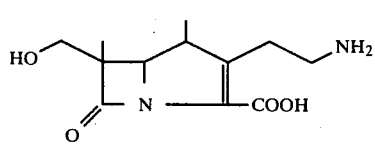

The carbapenem (10 mg) ester is dissolved in 1 ml dioxane. To the solution is added 1 ml water and 0.2 ml ethanol. The solution is adjusted to pH 3.5 with diluted HCl. One mg of 10% Pd/C is added. The mixture is hydrogenated for 20 min at 40 psi.

The mixture is filtered from catalyst, and the filtrate is extracted with 3×5 ml ether. The aqueous layer is separated and chromatographed on an XAD-2 column eluted with water to give the title compound 27.

EXAMPLE 4

Preparation of 1-methyl-2-cyclopropyl-6-(1-aminoethyl)-1-carbadethiapen-2-em-3-carboxylic acid

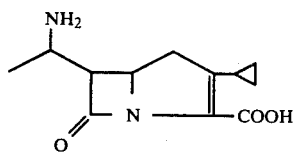

Step A

Preparation of 28

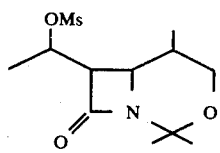

8-Oxo-2,2,5-trimethyl-7-(1-hydroxyethyl)-3-oxa-1-azabicyclo[4.2.0]octane (1.2 g) is treated with 1.1 equimolar amount of methanesulfonyl chloride and triethylamine at 0° C. in $CH_2Cl_2$ with stirring. After 30 min, the reaction mixture is washed with cold water, pH 7 phosphate buffer, dried over $MgSO_4$ and evaporated in vacuo. The residue is column chromatographed (silica gel EtOAc/cyclohexane 1:1) to give the product.

STEP B

Preparation of 29

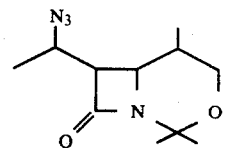

8-Oxo-2,2,5-trimethyl-(1-methanesulfonyloxyethyl)-3-oxa-1-azabicyclo[4.2.0]octane (2.81 g.) is suspended in 10 ml HMPA and treated with $NaN_3$ (0.78 g), at room temperature with stirring for 23 hours. The HMPA is removed in vacuo at 70°. The residue is dissolved in $CH_2Cl_2$, washed with $H_2O$, dried over $MgSO_4$ and evaporated in vacuo. Column chromatography (silica gel EtOAc/1:2) of the residue gives the product.

STEP C

Preparation of 30

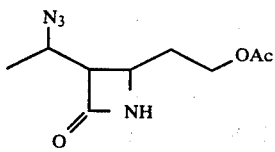

Compound 29 (1.31 g), is dissolved in 80 ml HOAc/$H_2O$ (4:1) and heated at 65° for 2.5 hrs. The HOAc and $H_2O$ is removed in vacuo. Benzene is added to the residue and evaporated to remove traces of water. The residue is then dissolved in 5.0 ml $CH_2Cl_2$, cooled to 0° C., and treated with 1.1 mole each of pyridine and acetyl chloride. The ice bath is removed 20 min after the mixing and stirring continues for another 20 min. After evaporated in vacuo, the residue is column chromatographed (silica gel, EtOAc/cyclohexane 1:1) to give the product.

STEP D

Preparation of 31

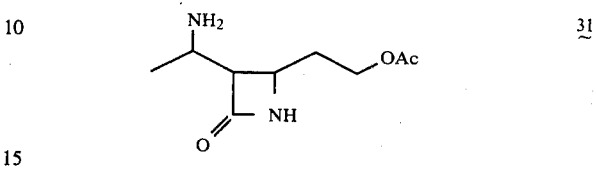

Trans-3-(1-azidoethyl)-4-(1-methyl-2'-acetoxyethyl)-2-azetidinone (0.824 g), is dissolved in EtOAc and hydrogenated with 0.824 g, 10% Pd/C under 40 lbs of $H_2$ for 1 hr. The catalyst is filtered off and the solution is evaporated in vacuo to give the product.

STEP E

Preparation of 32

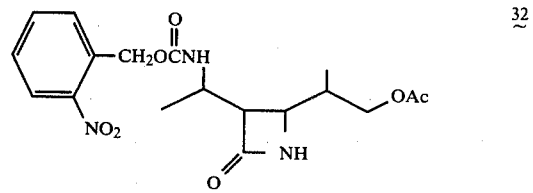

Trans and cis-3-(1-aminoethyl)-4-(1-methyl-2'-acetoxyethyl)-2-azetidinone (0.6575 g) is dissolved in 10 ml $CH_2Cl_2$, cooled to 0° C., and treated with 1.1 mole each of pyridine and o-nitrobenzyl chloroformate. The reaction mixture is stirred at 0° for 20 min, the ice bath is removed and stirring continued for another 30 min. The solution is diluted with $CH_2Cl_2$, washed with $H_2O$, dried and evaporated in vacuo. Column chromatography (silica gel, cyclohexane/EtOAc 1:1) of the residue gives the product.

Step F

Preparation of 33

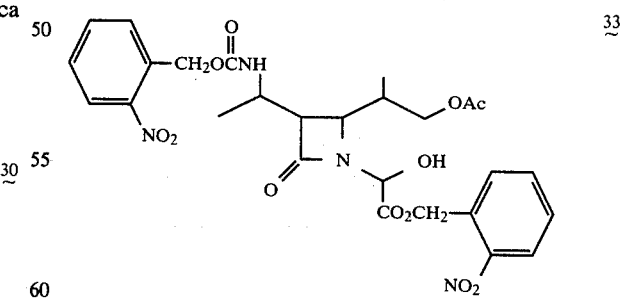

o-Nitrobenzyl glyoxalate prepared from (0.650 g), of di-o-nitrobenzyl tartarate, is dissolved in 20 ml benzene and refluxed using a Dean-Stark water separator containing $CaH_2$ for an hour. 3-(1-o-nitrobenzyloxycarbonylaminoethyl)-4-(1-methyl-2-acetoxyethyl)-2-azetidinone (0.580 g) is added and the mixture is refluxed for 8 hrs, cooled, evaporated. The residue is

STEP G

Preparation of 34

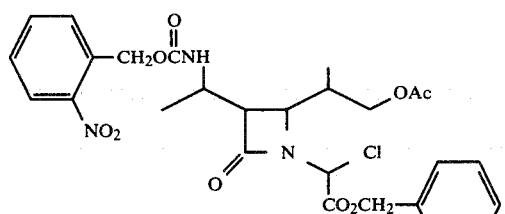

1-(o-nitrobenzyloxycarbonylhydroxymethyl)-3-(1-o-nitrobenzyloxycarbonylaminoethyl)-4-(1-methyl-2-acetoxyethyl)-2-acetidinone (0.775 g) is treated with 1.2 equimolar amount each of pyridine and $SOCl_2$ in THF at $-20°$. After 20 min, the cooling bath is removed and stirring continued for another 20 mins. The reaction mixture is diluted with benzene, filtered, and evaporated to give the chloro product which is used immediately in the next reaction.

STEP H

Preparation of 35

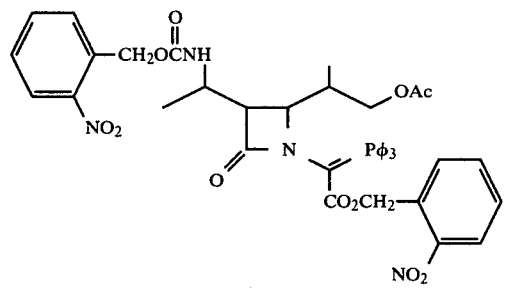

1-(o-nitrobenzyloxycarbonylchloromethyl)-3-(1-o-nitrobenzyloxycarbonylaminoethyl)-4-(1-methyl-2-acetoxyethyl)-2-azetidinone from above is dissolved in 4.0 ml DMF and treated with triphenylphosphine (0.414 g) in 3.0 ml DMF at 25° C. for 1.0 hr; DMF is removed under vacuum and the residue is taken up in $CHCl_3$, washed with pH 7 phosphate buffer, dried and evaporated. Column chromatography of the residue (silica gel, EtOAc/cyclohexane 1:1) gives the product.

STEP I

Preparation of 36

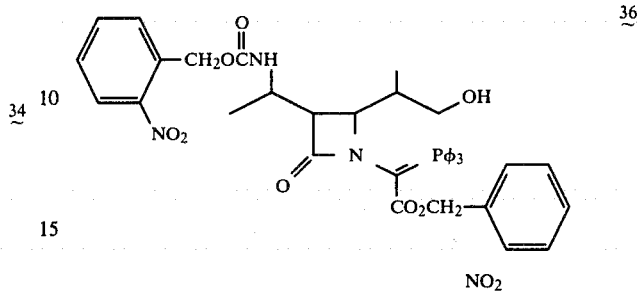

1-(o-nitrobenzyloxycarbonyltriphenylphosphoranylmethyl)-3-(1-o-nitrobenzyloxycarbonylaminoethyl)-4-(1-methyl-2-acetoxyethyl)-2-azetidinone (0.70 g) is dissolved in 10 ml abs. methanol and treated with sodium methoxide (0.050 g), at room temperature (25° C.) in $N_2$. The solution is stirred at r.t. for 1½ hr. After removal of MeOH in vacuo, the residue is taken up in $CH_2Cl_2$. The solution is washed with pH 7 phosphate buffer dried and evaporated. Column chromatography (silica gel, EtOAc/cyclohexane, 2:1) of the residue gives the product.

STEP J

Preparation of 37

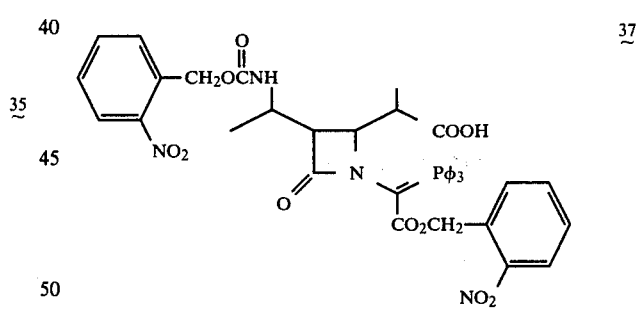

1-(o-Nitrobenzyloxycarbonyltriphenylphosphoranylmethyl)-3-(1-o-nitrobenzyloxycarbonylaminoethyl)-4-(1-methyl-2'-hydroxyethyl)-2-azetidinone (0.16 g) is dissolved in 5 ml acetone cooled to 0°. Jones Reagent (0.12 ml, 4 N solution) is added dropwise over 3 minutes and the resulting solution is stirred at 0° for 10 minutes. Isopropanol (0.05 ml) is added and the mixture stirred for another 2 minutes. The reaction mixture is diluted with $CH_2Cl_2$ and filtered. The filtrate is washed with saturated NaCl aqueous solution, dried and evaporated to give crude acid which is used without further purification in the next step.

STEP K

Preparation of 38

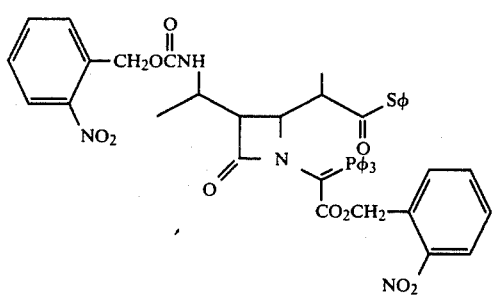

1-(o-nitrobenzyloxycarbonyltriphenylphosphoranylmethyl)-3-(1-o-nitrobenzyloxycarbonylaminoethyl)-4-(methylcarboxymethyl)-2-azetidinone (0.13 g) is dissolved in 5 ml CH$_2$Cl$_2$ and cooled to 0° under N$_2$. Oxalyl chloride (0.04 ml) is added dropwise over 5 minutes and then 1 drop of DMF is added. The mixture is stirred at 0° for 5 minutes and then at 25° C. for another 15 minutes. The solvent and excess oxalyl chloride are evaporated under reduced pressure. The residue is the desired acid chloride. 1-(o-nitrobenzyloxycarbonyltriphenylphosphoranylmethyl)-3-(1-o-nitrobenzyloxycarbonylaminoethyl)-4-(methylchlorocarbonylmethyl)-2-azetidinone is dissolved in 5 ml CH$_2$Cl$_2$ and cooled to 0° under N$_2$. Thiophenol (0.045 ml) is added and then pyridine (0.090 ml) is added dropwise. The reaction mixture is stirred at 0° for 5 minutes and then at 25° C. for 15 minutes, then diluted with CH$_2$Cl$_2$ and washed with water, dried and evaporated. The residue is chromatographed on silica gel using 50% EtOAc/C$_6$H$_6$ as eluant, to give the desired product (0.108 g).

STEP L

Preparation of 39

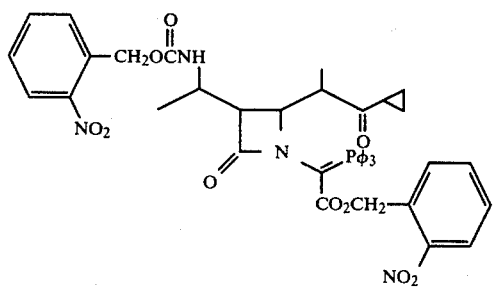

A solution of cyclopropyl magnesium bromide (0.25 m in Et$_2$O, 2.6 ml) is cooled to 0° under N$_2$. Cuprous iodide (61. mg) is added and the mixture is stirred at 0° for ½ hour. 1-(o-nitrobenzyloxycarbonyltriphenylphosphoranylmethyl)-3-(1-o-nitrobenzyloxycarbonylaminoethyl)-4-(methylphenylthiocarbonylmethyl)-2-azetidinone (64 mg) in 2 ml THF is added dropwise. The mixture is allowed to stir at 0° for 1 hour. A saturated NH$_4$Cl aqueous solution is added and the mixture is allowed to stir for 10 minutes. The organic phase is separated. The aqueous phase is extracted twice with CH$_2$Cl$_2$. The combined organic extracted is dried and evaporated. Preparative t.l.c. of the residue using silica gel and 50% EtOAc/benzene gives the desired product.

STEP M

Preparation of 40

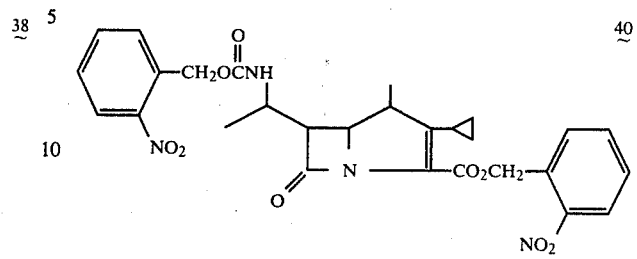

1-(o-nitrobenzyloxycarbonyltriphenylphosphoraranylmethyl)-3-1-(o-nitrobenzyloxycarbonylaminoethyl)-4-(methylcyclopropylcarbonylmethyl)-2-azetidinone (42 mg) is dissolved in 5 ml xylene, placed under N$_2$ and heated at 140° for 1 hour. The xylene is removed under reduced pressure and the residue is purified by preparative t.l.c. (silica gel G, 50% EtOAc/benzene) to give the desired product.

STEP N

Preparation of 41

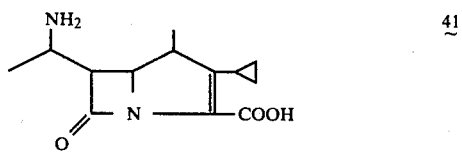

The product of Step M (1 mg) is dissolved in 2 ml p-dioxane, 0.2 ml EtOH and 2 ml H$_2$O. The mixture is hydrogenated under 1 atm H$_2$ in the presence of 10% Pd/C (1 ml) at 25° for 0.5 hr. The solution is extracted with 3 portions of 10 ml EtOAc and the aqueous solution is freeze dried to give 41.

EXAMPLE 5

Preparation of 42

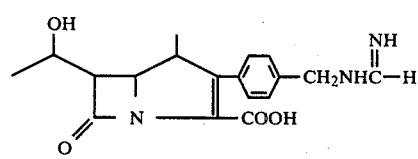

1-methyl-2-(p-aminomethylphenyl)-6-(1-hydroxyethyl)-1-carbadethia-pen-2-em-3-carboxylic acid (10 mg) dissolved in 10 ml 0.5 N phosphate buffer and 10 ml dioxane. At 0° C., the solution is maintained at pH 8.5–9.0 and treated with ethyl formimidoyl hydrochloride (20 mg). The mixture is stirred for 10 min, then is extracted with ether. The aqueous layer is separated and adjusted to pH 7.0 with diluted HCl then is chromatographed on a Dowex—50X8 (Na+) column eluting with water to give the desired product.

EXAMPLE 6

Following the procedures of the foregoing example, the following 1,2,6-substituted-1-carbadethiapen-2-em-3-carboxylic acid (I) are obtained. Remarks relative to the procedures are presented in the footnote to Table V.

TABLE V $$\underset{\underset{O}{\|}}{R^1\underset{}{\overset{R^2}{\diagdown}}}\!\!\!\!\!\!\!\!\!\!\!\!\!\underset{N}{\overset{R^4}{\diagdown}}\!\!\!\!\!\!\!\!\!\!\!\!\underset{\text{COOR}}{\overset{R^3}{\diagdown}} \qquad \text{I}$$

| Compound | R¹ | R² | R³ | R⁴ | R |
|---|---|---|---|---|---|
| (1.) | CH₃−CH(OH)− | H | −C₆H₄−CH₂NHC(=NH)CH₃ | CH₃ | H |
| (2.) | CH₃−CH(OH)− | H | −C₆H₄− (phenyl) | CH₃ | Na |
| (3.) | CH₃−CH(OH)− | H | −C₆H₄−NH₂ | CH₃ | H |
| (4.) | CH₃−CH(OH)− | H | −C₆H₄−CH₂NH₂ (meta) | CH₃ | H |
| (5.) | CH₃−CH(OH)− | H | −C₆H₄−CH₂NHC(=NH)−NH₂ | CH₃ | H |
| (6.) | CH₃−CH(OH)− | H | −CH₂CH₂NHC(=NH)−CH₃ | CH₃ | H |
| (7.) | CH₃−CH(OH)− | H | −CH(CH₃)CH₂CH₂NH₂ | CH₃ | H |
| (8.) | CH₃−CH(OH)− | H | −CH₂CH₂CH₂NHC(=NH)−H | CH₃ | H |
| (9.) | CH₃−CH(OH)− | H | −cyclopropyl−NH₂ | CH₃ | H |
| (10.) | CH₃−CH(OH)− | CH₃ | −cyclopropyl−NHCH=NH | CH₃ | H |
| (11.) | CH₃−CH(OH)− | CH₃ | −CH=CH−CH₂NHC(=NH)−CH₃ | C₂H₅ | H |
| (12.) | CH₃−CH(OH)− | H | −CH=CH−CH₂NHC(=NH)−CH₃ | C₂H₅ | H |
| (13.) | CH₃−CH(OH)− | H | −CH₂−(2-pyridyl) | CH₃ | H |
| (14.) | CH₃−CH(OH)− | H | −CH₂−(4-pyridyl) | CH₃ | H |
| (15.) | CH₃−CH(OH)− | H | −CH₂−(thiazolyl-CH₃) | CH₃ | Na |
| (16.) | −CH₂OH | H | −CH₂−(N-methyl-pyrrolidinyl) | CH₃ | H |
| (17.) | −CH₂OH | CH₃ | −C₆H₄−CH₂NH₂ | CH₃ | H |
| (18.) | −CH₂OH | CH₃ | −CH₂CH₂NHCH=NH | CH₃ | H |
| (19.) | CH₃−CH(NH₂)− | H | CH₃ | CH₃ | H |
| (20.) | CH₃−CH(NH₂)− | H | −C₆H₅ | CH₃ | H |
| (21.) | CH₃−CH(NH₂)− | H | −cyclopropyl | C₂H₅ | H |

TABLE V-continued

| | | | | | |
|---|---|---|---|---|---|
| (22.) | —CH$_2$NH$_2$ | CH$_3$ | —CH(CH$_3$)CH$_3$ | CH$_3$ | H |
| (23.) | C$_2$H$_5$\C(H)(NH$_2$)/H | H | -C$_6$H$_4$-OMe | CH$_3$ | H |
| (24.) | C$_2$H$_5$\C(H)(OH)/H | H | —CH$_2$CH(CH$_3$)—NH$_2$ | CH$_3$ | H |
| (25.) | (CH$_3$)$_2$CH—C(H)(OH)— | H | cyclopropyl-CH$_2$NH$_2$ | CH$_3$ | H |
| (26.) | (CH$_3$)$_2$CH—OH | H | 2-methyl-C$_6$H$_3$(CH$_2$NH$_2$)- | CH$_3$ | H |

FOOTNOTE TO TABLE V
(1.) Example 5, substitute ethylacetimidoyl hydrochloride for ethyl formimidoyl hydrochloride.
(2.) Example 2, Steps A-R, substitute phenylmagnesium bromide for p-tetrahydropyranyloxymethylphenylmagnesium bromide (THPPhMgBr) in Step N.
(3.) Example 2, Steps A-R, substitute p-tetrahydropyranyloxyphenylmagnesium bromide for THPPhMgBr in Step N.
(4.) Example 2, Steps A-R, substitute m-tetrahydropyranyloxymethylphenylmagnesium bromide for THPPhMgBr in Step N.
(5.) Example 5, substitute methylisouronium chloride for ethyl formimidoyl hydrochloride.
(6.) Example 2, Steps A-R, substitute tetrahydropyranyloxyethylmagnesium bromide for THPPhMgBr in Step N; Example 5, substitute acetimidoyl hydrochloride for formimidoyl hydrochloride.

(7.) Example 2, Steps A-R, substitute THP—OCH$_2$CH$_2$CH(CH$_3$)—MgBr for THPPhMgBr in Step N.

(8.) Example 2, Steps A-R substitute THP—OCH$_2$CH$_2$CH$_2$MgBr for THPPhMgBr in Step N; Example 5.

(9.) Example 2, Step A-R, substitute THP—O—cyclopropyl—MgBr for THPPhMgBr in Step N.

(10.) Example 3, Step A-P, substitute acetaldehyde for formaldehyde in Step B and THP—O—cyclopropyl—MgBr for THP—OCH$_2$CH$_2$MgBr in Step K; Example 5.

(11.) Example 2, Step A substitute 2-ethyl-2-butenal for 2-methyl-2-butanal; Example 3, Steps A-P, substitute 9-oxo-2,2,5,7-tetramethyl-3-oxa-1-azabicyclo[4.2.0]-octane in Step A, acetaldehyde for formaldehyde in Step B and THP—OCH$_2$CH=CHMgBr for THP—OCH$_2$CH$_2$MgBr in Step K; Example 5, substitute acetimidoyl hydrochloride formimidoyl hydrochloride.

(12.) Example 2, Steps A-R, substitute 2-ethyl-2-butenal for 2-methyl-2-butenal in Step A, and THP—OCH$_2$CH=CHMgBr for THPPhMgBr in Step K; Example 5, substitute acetimidoyl hydrochloride for formimidoyl hydrochloride.

(13.) Example 2, Steps A-R, substitute (pyridyl)-CH$_2$MgBr for THPPhMgBr in Step N.

(14.) Example 2, Steps A-R, substitute N-(pyridyl)-CH$_2$MgBr for THPPhMgBr in Step N.

(15.) Example 2, Steps A-R, substitute (thiazolyl)-CH$_2$MgBr for THPPhMgBr in Step N.

TABLE V-continued (16.) Example 2, Steps A–R, substitute formaldehyde for acetaldehyde in Step Fa and THPPhMgBr in Step N. 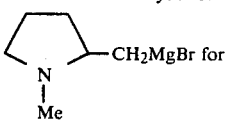

(17.) Example 3, Steps A–P, substitute THPOCH₂—⟨Ph⟩—MgBr for THP—CH₂CH₂CH₂MgBr in Step K.

(18.) Example 5, substitute the compound obtained from Example 3 for that obtained from Example 2.

(19.) Example 4, Steps A–N, substitute MeMgBr for ▷—MgBr in Step L.

(20.) Example 4, Steps A–N, substitute PhMgBr for ▷—MgBr Step L.

(21.) Example 2, Step A, substitute 2-ethyl-2-butenal for 2-methyl-2-butenal; Example 4, Steps A–N.

(22.) Example 3, Steps A–B; Example 4, Steps A–N, substitute (CH₃)₂CHMgBr for ▷—MgBr in Step L.

(23.) Example 2, Step Fa, substitute propanal for acetaldehyde; Example 4, Step A–N, substitute MeO—⟨Ph⟩—MgBr for ▷—MgBr in Step L.

(24.) Example 2, Steps A–R, substitute propanal for acetaldehyde in Step Fa and substitute THP—OCH(CH₃)—CH₂MgBr for THPPhMgBr in Step N.

(25.) Example 2, Steps A–R, substitute isobutanal for acetaldehyde in Step Fa and THP—OCH₂—△—MgBr for THPPhMgBr in Step N.

(26.) Example 2, Steps A–R, substitute BrMg—⟨Ph(CH₃)⟩—CH₂OTHP.

EXAMPLE 7

Preparation of Pharmaceutical Compositions

One such unit dosage form is prepared by mixing 120 mg of 1-methyl-1-carba-2-(p-aminomethylphenyl)-6-(1'-hydroxyethyl)-pen-2-em-3-carboxylic acid with 20 mg. of lactose and 5 mg. of magnesium stearate and placing the 145 mg. mixture into a No. 3 gelatin capsule. Similarly, by employing more of the active ingredient and less lactose, other dosage forms can be put up in No. 3 gelatin capsules and should it be necessary to mix more than 145 mg. of ingredients together, larger capsules such as compressed tablets and pills can also be prepared. The following examples are illustrative of the preparation of pharmaceutical formulations:

| TABLET | PER TABLET |
|---|---|
| 1-methyl-1-carba-2-(p-aminomethylphenyl)-6-(1'-hydroxyethyl)-pen-2-em-3-carboxylic acid | 125 mg. |
| Cornstarch, U.S.P. | 6 mg. |
| Dicalcium Phosphate | 192 mg. |
| Lactose, U.S.P. | 190 mg. |
| Magnesium Stearate | Balance |

The active ingredient is blended with the dicalcium phosphate, lactose and about half of the cornstarch. The mixture is then granulated with 15% cornstarch paste (6 mg.) and rough-screened. It is dried at 45° C. and screened again through No. 16 screens. The balance of the cornstarch and the magnesium stearate is added and the mixture is compressed into tablets, approximately 0.5 inch in diameter each weighing 800 mg.

| PARENTERAL SOLUTION | | |
|---|---|---|
| Ampoule: | | |
| 1-methyl-1-carba-2-(p-aminomethylphenyl)-6-(1'-hydroxyethyl)-pen-2-em-3-carboxylic acid | | 500 mg. |
| Sterile water | | 2 ml. |
| OPTHALMIC SOLUTION | | |
| 1-methyl-1-carba-2-(p-aminomethylphenyl)-6-(1'-hydroxyethyl)-pen-2-em-3-carboxylic acid | | 100 mg. |
| Hydroxypropylmethyl cellulose | | 5 mg. |
| Sterile water | to | 1 ml. |
| θTIC SOLUTION | | |
| 1-methyl-1-carba-2-(p-aminomethylphenyl)-6-(1'-hydroxyethyl)-pen-2-em-3-carboxylic acid | | 100 mg. |
| Benzalkonium chloride | | 0.1 mg. |
| Sterile water | to | 1 ml. |
| TOPICAL OINTMENT | | |
| 1-methyl-1-carba-2-(p-aminomethylphenyl)-6-(1'-hydroxyethyl)-pen-2-em-3-carboxylic acid | | 100 mg. |
| Polyethylene glycol 4000 U.S.P. | | 400 mg. |
| Polyethylene glycol 400 U.S.P. | | 1.0 gram. |

The active ingredient in the above formulations may be administered alone or in combination with other biologically active ingredients as, for example, with other antibacterial agents such as lincomycin, a penicillin, streptomycin, novobiocin, gentamicin, neomycin, colistin and kanamycin, or with other therapeutic agents such as probenecid.

What is claimed is:

1. A compound having the structure:

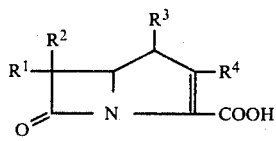

and the pharmaceutically acceptable salts thereof; wherein $R^1$, $R^2$, $R^3$ and $R^4$ are independently selected from the group consisting of hydrogen ($R^3$ is not hydrogen), and substituted and unsubstituted: alkyl having 1-6 carbon atoms, alkenyl and alkynyl having 2-6 carbon atoms, aryl and aralkyl having 6-10 ring carbon atoms and 1-6 carbon atoms in the alkyl chain, cycloalkyl and cycloalkylalkyl having 3 to 6 ring carbon atoms and 1-6 carbon atoms in the alkyl moiety; wherein the substituents on $R^1$, $R^2$, $R^3$ and $R^4$ are selected from chloro, bromo, fluoro, hydroxyl, amino, mono-, di- and trialkyl substituted amino (each alkyl having 1-6 carbon atoms) alkoxyl having 1-6 carbon atoms, guanidino, cyano, amidino and carboxyl; with the proviso that $R^4$ is not hydrogen.

2. A compound having the structure:

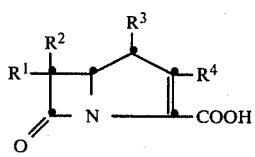

and the pharmaceutically acceptable salts thereof; wherein $R^3$ and $R^4$ are alkyl, cyclopropyl, benzyl or phenyl; $R^1$ is hydrogen and $R^2$ is alkyl or phenylalkyl substituted by hydroxyl or amino.

3. A compound according to claim 2 wherein $R^3$ and $R^4$ are methyl, ethyl, isopropyl, t-butyl or phenyl and $R^2$ is 1-hydroxyethyl, methyl, or hydroxymethyl.

4. A compound having the structure:

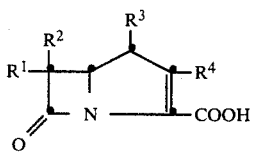

and the pharmaceutically acceptable salts thereof: wherein $R^4$ is selected from the group consisting of:

—CH$_2$CH$_2$CH$_2$NH$_2$, —CH$_2$CH$_2$NH$_2$, —CH$_3$, —CH$_2$CH$_2$CH$_2$OH,

—CH$_2$CH$_2$COOH, —C$_6$H$_4$—SCH$_3$, —CH$_2$CH=CH—SCH$_3$,

—C$_6$H$_4$—OCH$_3$, —CH=CHCH$_2$CH$_2$NH$_2$,

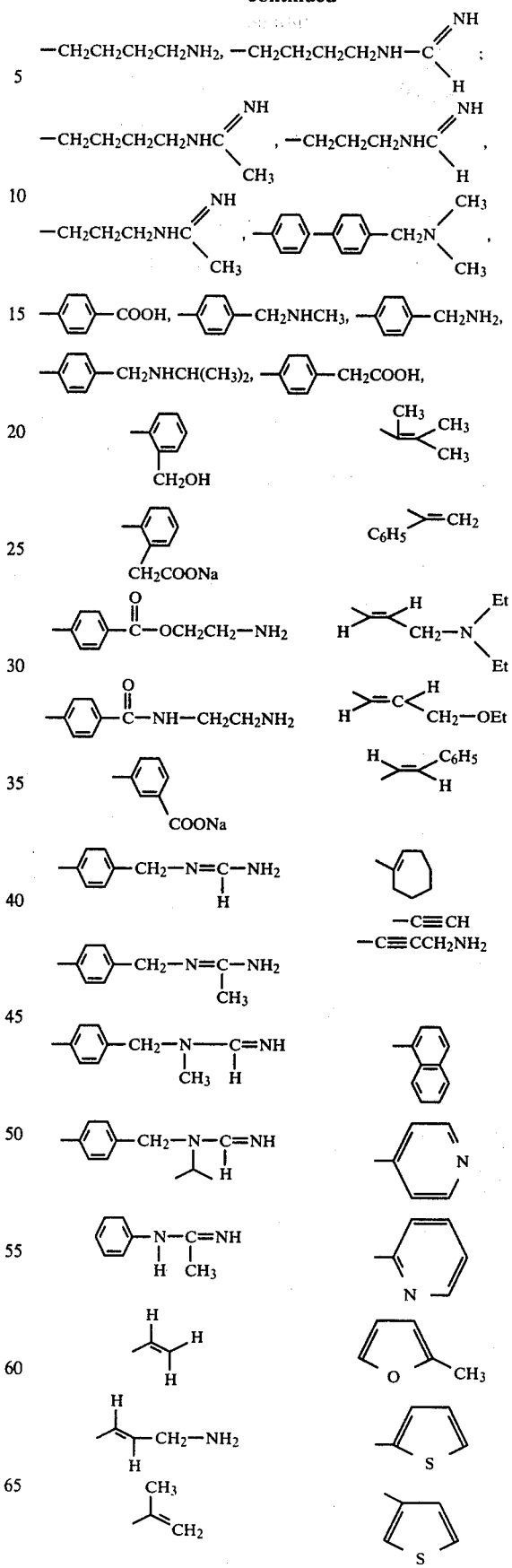

-continued

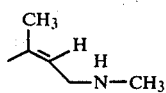
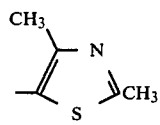
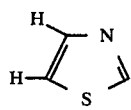
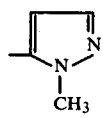
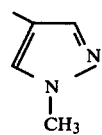
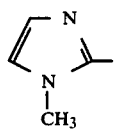

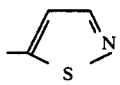

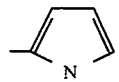
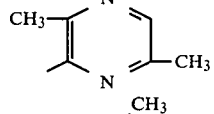
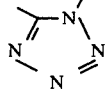

and wherein $R^1$, $R^2$ and $R^3$ are independently selected from the group consisting of hydrogen ($R^3$ is not hydrogen), and substituted and unsubstituted: alkyl having 1–6 carbon atoms, alkenyl and alkynyl having 2–6 carbon atoms, aryl and aralkyl having 6–10 ring carbon atoms and 1–6 carbon atoms in the alkyl chain, cycloalkyl and cycloalkylalkyl having 3–6 ring carbon atoms and 1–6 carbon atoms in the alkyl moiety; wherein the substituents on $R^1$, $R^2$, and $R^3$ are selected from chloro, bromo, fluoro, hydroxyl, amino, mono-, di- and trialkyl substituted amino (each alkyl having 1–6 carbon atoms) alkoxyl having 1–6 carbon atoms, guanidino, cyano, amidino, and carboxyl.

5. A compound according to claim 4 wherein $R^3$ is alkyl having 1–6 carbon atoms or phenyl.

6. An antibiotic pharmaceutical composition comprising a therapeutically effective amount of a compound according to claims 1, 2, 3, 4 or 5 and a pharmaceutical carrier therefor.

* * * * *